United States Patent
Suh et al.

(10) Patent No.: US 9,925,243 B2
(45) Date of Patent: *Mar. 27, 2018

(54) CHIMERIC FIBROBLAST GROWTH FACTOR (FGF) 2/FGF1 PEPTIDES AND METHODS OF USE

(71) Applicant: Salk Institute for Biological Studies, La Jolla, CA (US)

(72) Inventors: Jae Myoung Suh, San Diego, CA (US); Michael Downes, San Diego, CA (US); Ronald M. Evans, La Jolla, CA (US); Annette Atkins, San Diego, CA (US); Senyon Choe, Solana Beach, CA (US); Witek Kwiatkowski, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/092,481

(22) Filed: Apr. 6, 2016

(65) Prior Publication Data

US 2016/0206695 A1    Jul. 21, 2016

Related U.S. Application Data

(63) Continuation of application No. PCT/US2014/061593, filed on Oct. 21, 2014.

(60) Provisional application No. 61/893,696, filed on Oct. 21, 2013.

(51) Int. Cl.
| | | |
|---|---|---|
| *A61K 38/18* | (2006.01) | |
| *C07K 14/50* | (2006.01) | |
| *A61K 45/06* | (2006.01) | |
| *A61K 38/00* | (2006.01) | |

(52) U.S. Cl.
CPC .......... *A61K 38/1825* (2013.01); *A61K 45/06* (2013.01); *C07K 14/50* (2013.01); *C07K 14/501* (2013.01); *C07K 14/503* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 5,132,408 A | 7/1992 | Baird et al. |
|---|---|---|
| 5,478,804 A | 12/1995 | Calabresi et al. |
| 5,885,960 A | 3/1999 | Nies |
| 6,326,484 B1 | 12/2001 | Gage et al. |
| 6,982,170 B1 | 1/2006 | Maciag et al. |
| 7,491,697 B2 | 2/2009 | Beals et al. |
| 7,582,607 B2 | 9/2009 | Frye et al. |
| 7,595,296 B1 | 9/2009 | Blaber et al. |
| 7,622,445 B2 | 11/2009 | Frye et al. |
| 7,655,627 B2 | 2/2010 | Frye et al. |
| 7,700,558 B2 | 4/2010 | Thomason et al. |
| 7,723,050 B2 | 5/2010 | Urdea et al. |
| 7,776,825 B1 | 8/2010 | Blaber et al. |
| 7,790,682 B1 | 9/2010 | Blaber et al. |
| 7,956,033 B2 | 6/2011 | Cheng et al. |
| 8,053,408 B2 | 11/2011 | Thomason et al. |
| 8,168,591 B2 | 5/2012 | Takada et al. |
| 8,372,952 B2 | 2/2013 | Smith et al. |
| 8,535,912 B2 | 9/2013 | Sonoda |
| 8,642,546 B2 | 2/2014 | Belouski et al. |
| 8,889,426 B2 | 11/2014 | Mohammadi et al. |
| 8,889,621 B2 | 11/2014 | Mohammadi et al. |
| 8,906,854 B2 | 12/2014 | Jonker et al. |
| 8,951,966 B2 | 2/2015 | Ling et al. |
| 8,999,929 B2 | 4/2015 | Mohammadi et al. |
| 9,072,708 B2 | 7/2015 | Jonker et al. |
| 9,272,017 B2 | 3/2016 | Mohammadi et al. |
| 9,446,097 B2 | 9/2016 | Jonker et al. |
| 9,464,126 B2 | 10/2016 | Mohammadi et al. |
| 9,474,785 B2 | 10/2016 | Mohammadi et al. |
| 2003/0008820 A1 | 1/2003 | Kwan et al. |
| 2004/0082564 A1 | 4/2004 | Arrhenius et al. |
| 2005/0227329 A1 | 10/2005 | Fiddes et al. |
| 2006/0217310 A1 | 9/2006 | Chiu et al. |
| 2007/0099834 A1 | 5/2007 | Takada et al. |
| 2008/0176790 A1 | 7/2008 | DeFrees |
| 2008/0260703 A1 | 10/2008 | Riordan et al. |

(Continued)

FOREIGN PATENT DOCUMENTS

| CA | 2 390 285 A1 | 12/2003 |
|---|---|---|
| CN | 1890371 A | 1/2007 |

(Continued)

OTHER PUBLICATIONS

Adams et al., "LY2405319, an Engineered FGF21 Variant, Improves the Metabolic Status of Diabetic Monkeys," *PLoS One* 8:e65763, 2013.

(Continued)

*Primary Examiner* — Marianne P Allen

(74) *Attorney, Agent, or Firm* — Klarquist Sparkman, LLP

(57) ABSTRACT

The present disclosure provides chimeric proteins having an N-terminus coupled to a C-terminus, wherein the N-terminus comprises an N-terminal portion of fibroblast growth factor (FGF) 2 and the C-terminus comprises a portion of an FGF1 protein, wherein the chimeric protein comprises at least 95% sequence identity to SEQ ID NO: 9, 10, 11, 12 or 13. Also provided are nucleic acid molecules that encode such proteins, and vectors and cells that include such nucleic acids. Methods of using the disclosed molecules to reduce blood glucose levels are also provided.

32 Claims, 1 Drawing Sheet

(56) References Cited

U.S. PATENT DOCUMENTS

| | | |
|---|---|---|
| 2010/0062984 A1 | 3/2010 | Kumar et al. |
| 2010/0158914 A1 | 6/2010 | Desnoyers |
| 2010/0184665 A1 | 7/2010 | Suzuki et al. |
| 2010/0286042 A1 | 11/2010 | Imamura et al. |
| 2011/0053841 A1 | 3/2011 | Yayon et al. |
| 2011/0150901 A1 | 6/2011 | Smith et al. |
| 2011/0172401 A1 | 7/2011 | Cujec et al. |
| 2011/0195077 A1 | 8/2011 | Glass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0130983 A1 | 5/2013 | Blaber et al. |
| 2013/0184211 A1 | 7/2013 | Mohammadi et al. |
| 2013/0197191 A1 | 8/2013 | Smith et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0065419 A1 | 3/2015 | Jonker et al. |
| 2015/0111821 A1 | 4/2015 | Suh et al. |
| 2015/0343022 A1 | 12/2015 | Jonker et al. |
| 2016/0237133 A1 | 8/2016 | Suh et al. |
| 2016/0354440 A1 | 12/2016 | Jonker et al. |
| 2017/0056475 A1 | 3/2017 | Jonker et al. |

FOREIGN PATENT DOCUMENTS

| | | |
|---|---|---|
| EP | 0 420 222 A1 | 4/1991 |
| EP | 0 645 451 B1 | 8/2001 |
| WO | WO 1996/036362 A1 | 11/1996 |
| WO | WO 1999/055861 A2 | 11/1999 |
| WO | WO 2001/013031 A2 | 2/2001 |
| WO | WO 2001/098346 A2 | 12/2001 |
| WO | WO 2002/036732 A2 | 5/2002 |
| WO | WO 03/052378 A2 | 6/2003 |
| WO | WO 2004/003179 A1 | 1/2004 |
| WO | WO 2004/069298 A1 | 8/2004 |
| WO | WO 2004/108167 A1 | 12/2004 |
| WO | WO 2005/063807 A2 | 7/2005 |
| WO | WO 2006/028714 A1 | 3/2006 |
| WO | WO 2008/038287 A2 | 4/2008 |
| WO | WO 2008/047235 A2 | 4/2008 |
| WO | WO 2010/075037 A1 | 7/2010 |
| WO | WO 2010/129600 A2 | 11/2010 |
| WO | WO 2010/135491 A2 | 11/2010 |
| WO | WO 2011/047267 A1 | 4/2011 |
| WO | WO 2011/068893 A1 | 6/2011 |
| WO | WO 2011/130729 A2 | 10/2011 |
| WO | WO 2012/010553 A1 | 1/2012 |
| WO | WO 2012/062078 A1 | 5/2012 |
| WO | WO 2012/066075 A1 | 5/2012 |
| WO | WO 2012/140650 A2 | 10/2012 |
| WO | WO 2012/158244 A2 | 11/2012 |
| WO | WO 2013/006486 A2 | 1/2013 |
| WO | WO 2013/033452 A2 | 3/2013 |
| WO | WO 2013/090919 A1 | 6/2013 |
| WO | WO 2013/131091 A1 | 9/2013 |
| WO | WO 2013/184958 A1 | 12/2013 |
| WO | WO 2013/184960 A2 | 12/2013 |
| WO | WO 2013/184962 A1 | 12/2013 |
| WO | WO 2014/085365 A2 | 6/2014 |
| WO | WO 2014/198003 A1 | 12/2014 |
| WO | WO 2015/061331 A1 | 4/2015 |
| WO | WO 2015/061351 A1 | 4/2015 |
| WO | WO 2015/061361 A1 | 4/2015 |
| WO | WO 2015/065897 A1 | 5/2015 |
| WO | WO 2015/149069 A1 | 10/2015 |
| WO | WO 2015/183890 A2 | 12/2015 |
| WO | WO 2016/089945 A1 | 6/2016 |
| WO | WO 2016/100820 A2 | 6/2016 |
| WO | WO 2016/172153 A2 | 10/2016 |
| WO | WO 2016/172156 A2 | 10/2016 |
| WO | WO 2016/172290 A1 | 10/2016 |

OTHER PUBLICATIONS

Liu et al., "Effective Treatment of Steatosis and Steatohepatitis by Fibroblast Growth Factor 1 in Mouse Models of Nonalcoholic Fatty Liver Disease," *Proc Natl Acad Sci USA* 113:2288-2293, 2016.

Luo et al., "A Nontumorigenic Variant of FGF19 Treats Cholestatic Liver Diseases," *Sci Transl Med*. 6:247ra100, 2014.

Ohta and Itoh, "Roles of FGFs as Adipokines in Adipose Tissue Development, Remodeling, and Metabolism," Frontiers in Endocrinology, vol. 5, No. FEB, Article 18, pp. 1-4, 2014.

Zhou et al., "Separating Tumorigenicity from Bile Acid Regulatory Activity for Endocrine Hormone FGF19," *Cancer Res*. 74:3306-3316, 2014.

Brewster et al., "Heparin-independent mitogenicity in an endothelial and smooth muscle cell chimeric growth factor (S130K-HBGAM)," *Am J Surg* 188:575-579, 2004.

Brewster et al., "Improving endothelial healing with novel chimeric mitogens," *Am J Surg*. 192:589-593, 2006.

Klingenberg et al., "Effects of Mutations of a Phosphorylation Site in an Exposed Loop in Acidic Fibroblast growth Factor," *J Biol Chem*. 274:18081-18086, 1999.

Shireman et al., "The S130K fibroblast growth factor-1 mutant induces heparin-independent proliferation and is resistant to thrombin degradation in fibrin glue," *J Vasc Surg*. 31:382-390, 2000.

Beenken and Mohammadi, "The FGF Family: Biology, Pathophysiology and Therapy," *Nat Rev Drug Discov*. 8:235-253, 2009.

Bossard et al., "Translokin is an Intracellular Mediator of FGF-2 Trafficking," *Nat Cell Biol*. 5:433-439, 2003.

Brych et al., "Structure and Stability Effects of Mutations Designed to Increase the Primary Sequence Symmetry Within the Core Region of a β-Trefoil," *Prot Sci*. 10:2587-2599, 2001.

Czajkowsky et al., "Fc-Fusion Proteins: New Developments and Future Perspectives," *EMBO Mol Med*. 4:1015-1028, 2012.

Dubey et al., "Spackling the Crack: Stabilizing Human Fibroblast Growth Factor-1 by Targeting the N and C Terminus β-Strand Interactions," *J Mol Biol*. 371:256-268, 2007.

Dutchak et al., "Fibroblast Growth Factor-21 Regulates PPARγ Activity and the Antidiabetic Actions of Thiazolidinediones," *Cell* 148:556-567, 2012.

Fowler, "Diabetes Treatment, Part 2: Oral Agents for Glycemic Management," *Clin. Diabetes* 25:131-134, 2007.

Goetz et al., "Conversion of a Paracrine Fibroblast Growth Factor into an Endocrine Fibroblast Growth Factor," *J Biol Chem*. 287:29134-29146, 2012.

Hevener et al., "Muscle-Specific Pparg Deletion Causes Insulin Resistance," *Nat Med*. 9:1491-1497 (2003).

Hutley et al., "Fibroblast Growth Factor 1," *Diabetes* 53:3097-3106, 2004.

Ikezono and Hanai, "The Effect of Satiation of the Acidic Fibroblast Growth Factor-Like Activity on Ingestion of Soyamalt and Soybean Milk"; *Int J Obesity* 25(S2):S142, 2001. Abstract p. 403.

Imamura et al., "Recovery of Mitogenic Activity of a Growth Factor Mutant with a Nuclear Translocation Sequence," *Science* 249:1567-1570, 1990.

Imamura et al., "Identification of the Domain Within Fibroblast Growth Factor-1 Responsible for Heparin-Dependence," *Biochim Biophys Acta*. 1266:124-130, 1995.

Inchovska et al., "Fibroblast Growth Factors Promote Pancreatic Cell Proliferation in Normal and STZ-Treated Hamsters," *Arch Med Sci*. 2:90-93, 2006.

Inchovska et al., "Role of FGF1, FGF2, FGF7 in the Development of Pancreas from Control and Streptozotocin-Treated Hamsters," *Cell Proliferation* 39:537-550, 2006.

Inchovska et al., "Role of FGF1, FGF2 and FGF7 in the Development of the Pancreas of Diabetic Hamsters," *Acta morphologica et anthropologica* 12:79-85, 2007.

(56) References Cited

OTHER PUBLICATIONS

Itoh and Ornitz, "Fibroblast Growth Factors: From Molecular Evolution to Roles in Development, Metabolism and Disease," *J Biochem.* 149:121-130, 2011.
Jonker et al., "A PPARγ-FGF1 Axis is Required for Adaptive Adipose Remodelling and Metabolic Homeostasis," *Nature* 485:391-394, 2012.
Kharitonenkov et al., "FGF-21 as a Novel Metabolic Regulator," *J Clin Invest.* 115:1627-1635, 2005.
Kilkenny et al.; "Fibroblast Growth Factor Receptor-1 Signaling in Pancreatic Islet Beta-Cells is Modulated by the Extracellular Matrix," *Mol EndocrinoL.* 22:196-205, 2008.
Kobielak et al., "Protease Resistant Variants of FGF1 with Prolonged Biological Activity," *Protein Pept Lett.* 21:434-443, 2014.
Lee and Blaber, "The Interaction Between Thermodynamic Stability and Buried Free Cysteines in Regulating the Functional Half-Life of Fibroblast Growth Factor-1," *J Mol Biol.* 393:113-127, 2009.
Lee and Blaber, "Structural Basis of Conserved Cysteine in the Fibroblast Growth Factor Family: Evidence for a Vestigial Half-Cystine," *J Mol Biol.* 393:128-139, 2009.
Lehrke and Lazar, "The Many Faces of PPARγ," *Cell* 123:993-999, 2005.
Li et al., "Strong Suppression of Feeding by a Peptide Containing Both the Nuclear Localization Sequence of Fibroblast Growth Factor-1 and a Cell Membrane-Permeable Sequence," *Neuroscience Lett.* 255:41-44, 1998.
Lin et al., "Role of the Nuclear Localization Sequence in Fibroblast Growth Factor-1-Stimulated Mitogenic Pathways," *J Biol Chem.* 271:5305-5308, 1996.
Mori et al., "Direct Binding of Integrin αvβ3 to FGF1 Plays a Role in FGF1 Signaling," *J Biol Chem* 283:18066-18075, 2008.
Motomura et al., "An FGF1:FGF2 Chimeric Growth Factor Exhibits Universal FGF Receptor Specificity, Enhanced Stability and Augmented Activity Useful for Epithelial Proliferation and Radioprotection," *Biochim Biophys Acta.* 1780:1432-1440, 2008.
Nakayama et al., "Post Treatment With an FGF Chimeric Growth Factor Enhances Epithelial Cell Proliferation to Improve Recovery From Radiation-Induced Intestinal Damage," *Int J Radiat Oncol Biol Phys.* 78:860-867, 2010.
Niu et al., "Solid-Phase Polyethylene Glycol Conjugation Using Hydrophobicinteraction Chromatography," *J Chromatogr. A* 1327:66-72, 2014.
Ogneva et al., "The Effect of In Vitro Fibroblast Growth Factors on Cell Proliferation in Pancreas from Normal and Streptozoticin-Treated Rats," *Diabetes Res Clin Practice* 57:11-16, 2002.
Reid, "Choosing GLP-1 Receptor Agonists or DPP-4 Inhibitors: Weighing the Clinical Trial Evidence," *Clin. Diabetes* 30:3-12, 2012.
Ripsin et al., "Management of Blood Glucose in Type 2 Diabetes Mellitus," *Am Fam. Physician* 79:29-36, 2009.
Sasaki et al., "Effects of Fibroblast Growth Factors and Related Peptides on Food Intake by Rats," *Physiol Behav.* 56:211-218, 1994.
Smith et al., "FGF21 Can Be Mimicked In Vitro and In Vivo by a Novel Anti-FGFR1c/b-Klotho Bispecific Protein," *PLoS ONE* 8:e61432, 2013.
Suh et al., "Endocrinization of FGF1 Produces a Neomorphic and Potent Insulin Sensitizer," *Nature* 513:436-439, 2014.
Sun and Scherer, "The PPARγ-FGF1 Axis: An Unexpected Mediator of Adipose Tissue Homeostasis," *Cell Res.* 22:1416-1418, 2012.
Suzuki et al., "Feeding Suppression by Fibroblast Growth Factor-1 is Accompanied by Selective Induction of Heat Shock Protein 27 in Hypothalamic Astrocytes," *Eur J Neurosci.* 13:2299-2308, 2001.
Van Dijk et al., "Quantification of Hepatic Carbohydrate Metabolism in Conscious Mice Using Serial Blood and Urine Spots," *Anal Biochem.* 322:1-13, 2003.
Wang et al., "A Novel Monoclonal Antibody to Fibroblast Growth Factor 2 Effectively Inhibits Growth of Hepatocellular Carcinoma Xenografts," *Mol Cancer Ther.* 11:864-872, 2012.

Wei et al., "Fibroblast Growth Factor 21 Promotes Bone Loss by Potentiating the Effects of Peroxisome Proliferator-Activated Receptor γ," *Proc Natl Acad Sci. USA* 109:3143-3148, 2012.
Widberg et al., "Fibroblast Growth Factor Receptor 1 is a Key Regulator of Early Adipogenic Events in Human Preadipocytes"; *Am J Physiol Endocrinol Metab.* 296:E121-E131, 2009.
Wu et al., "Separating Mitogenic and Metabolic Activities of Fibroblast Growth Factor 19 (FGF19)," *Proc Natl Acad Sci U.S.A.* 107:14158-14163, 2010.
Wu et al., "Amelioration of Type 2 Diabetes by Antibody-Mediated Activation of Fibroblast Growth Factor Receptor 1," *Sci Transl Med.* 3:113ra126, 2011.
Wu and Li, "Chapter 13—Understanding the Structure-Function Relationship Between Fgf19 and Its Mitogenic and Metabolic Activities," in *Endocrine FGFs and Klothos*, Makoto Kuro-o (ed.), pp. 195-213, Landes Bioscience and Springer Science+Business Media, 2012.
Xia et al., "Pharmacokinetic Properties of 2nd-Generation Fibroblast Growth Factor-1 Mutants for Therapeutic Application," *PLoS One* 7:e48210, 2012.
Youseff et al., "Diabetes Mellitus, Obesity, and Hepatic Steatosis," *Semin Gastrointest Dis.* 13:17-30, 2002.
Zakrzewska et al., "Design of Fully Acctive FGF-1 Variants with Increased Stability," *Protein Eng Des Sel.* 17:603-611, 2004.
Zakrzewska et al., "Increased Protein Stability of FGF1 Can Compensate for Its Reduced Affinity for Heparin," *J Biol Chem.* 284:25388-25403, 2009.
Zhu et al., "Three-Dimensional Structures of Acidic and Basic Fibroblast Growth Factors," *Science* 251:90-93, 1991.
Zinn et al., "Imaging Tc-99m-Labeled FGF-1 Targeting in Rats," *Nucl Med Biol.* 27:407-414, 2000.
Fathallah et al., "Drug-Induced Hyperglycaemia and Diabetes," *Drug Safety* 38:1153-1168, 2015.
Guo et al., "Risk of Diabetes Mellitus Associated With Atypical Antipsychotic Use Among Patients With Bipolar Disorder: A Retrospective, Population-Based, Case-Control Study", *J Clin. Psychiatry* 67:1055-1061, 2006.
Perez et al., "Glucocorticoid-induced hyperglycemia", *J. Diabetes* 6:9-20, 2014.
Tamez-Perez et al., "Steroid hyperglycemia: Prevalence, early detection and therapeutic recommendations: A narrative review", *World J. Diabetes* 6:1073-1081, 2015.
Van Raalte & Diamant, "Steroid diabetes: from mechanism to treatment?", *Neth J Med.* 72:62-72, 2014.
Abraham et al., "Human Basic Fibroblast Growth Factor: Nucleotide Sequence and Genomic Organization," *EMBO J.* 5(10): 2523-2528, 1986.
Andrukhova et al., "FGF23 Acts Directly on Renal Proximal Tubules to Induce Phosphaturia Through Activation of the ERK1/2-SKG1 Signaling Pathway," *Bone* 51:621-628, 2012.
Beenken & Mohammadi, "The Structural Biology of the FGF19 Subfamily," *Adv Exp Med Biol.* 728:1-24, 2012.
Beenken et al., "Plasticity in Interactions of Fibroblast Growth Factor 1 (FGF1) N Terminus With FGF Receptors Underlies Promiscuity of FGF1," *J Biol Chem.* 287:3067-3078, 2012.
Beenken, "Structural and biochemical Studies of FGF-FGFR Complexes," Thesis, Sep. 2011.
Cassidy et al., "Elevated Frequency of Diabetes Mellitus in Hospitalized Manic-Depressive Patients," *Am J Psychiatry* 156:1417-1420, 1999.
Esch et al., "Primary Structure of Bovine Pituitary Basic Fibroblast Growth Factor (FGF) and Comparison with the Amino-Terminal Sequence of Bovine Brain Acidic FGF," *PNAS* 82:6507-6511, 1985.
Finan et al., "A Rationally Designed Monomeric Peptide Triagonist Corrects Obesity and Diabetes in Rodents," *Nat Med.* 21:27-36, 2015.
Ge et al., "Characterization of a FGF19 Variant with Altered Receptor Specificity Revealed a Central Role for FGFR1c in the Regulation of Glucose Metabolism," *PloS ONE* 7:e33603, 2012.
Goetz et al., "Isolated C-Terminal Tail of FGF23 Alleviates Hypophosphatemia by Inhibiting FGF23-FGFR-Klotho Complex Formation," *Proc Natl Acad Sci USA* 107:407-412, 2010.

(56) References Cited

OTHER PUBLICATIONS

Goetz et al., "Klotho Coreceptors Inhibit Signaling by Paracrine Fibroblast Growth Factor 8 Subfamily Ligands," *Mol Cell Biol.* 32:1944-1954, 2012.
Goetz et al., "Molecular Insights Into the Klotho-Dependent, Endocrine Mode of Action of Fibroblast Growth Factor 19 Subfamily Members," *Mol Cell Biol.* 27:3417-3428, 2007.
Hwang and Weis, "Steroid-Induced Diabetes: A Clinical and Molecular Approach to Understanding and Treatment," *Diabetes Metab Res Rev.* 30:96-102, 2014.
Igarashi et al., "Characterization of Recombinant Human Fibroblast Growth Factor (FGF)-10 Reveals Functional Similarities with Keratinocyte Growth Factor (FGF-7)," *J Biol Chem.* 273:13230-13235, 1998.
Irwin et al., "A Novel CCK-8/GLP-1 Hybrid Peptide Exhibiting Prominent Insulinotropic, Glucose-Lowering, and Satiety Actions With Significant Therapeutic Potential in High-Fat-Fed Mice," *Diabetes* 64:2996-3009, 2015.
Kharitonenkov et al., "FGF-21/FGF-21 Receptor Interaction and Activation is Determined by βKlotho," *J Cell Physiol.* 215:1-7, 2008.
Kharitonenkov et al., "The Metabolic State of Diabetic Monkeys is Regulated by Fibroblast Growth Factor-21," *Endocrinology* 148:774-781, 2007.
Kurosu et al., "The Klotho Gene Family as a Regulator of Endocrine Fibroblast Growth Factors," *Mol Cell Endocrin.* 299:72-78, 2009.
Kurosu et al., "Tissue-Specific Expression of βKlotho and Fibroblast Growth Factor (FGF) Receptor Isoforms Determines Metabolic Activity of FGF19 and FGF21," *J Biol Chem.* 282:26687-26695, 2007.
Micanovic et al., "Different Roles of N- and C-Termini in the Functional Activity of FGF21," *J Cell Physiol.* 219:227-234, 2009.
Mohammadi et al., "Structural Basis for Fibroblast Growth Factor Receptor Activation," *Cytokine Growth Factor Rev.* 16:107-137, 2005.
O'Harte et al., "Novel Dual Agonist Peptide Analogues Derived From Dogfish Glucagon Show Promising in vitro Insulin Releasing Actions and Antihyperglycaemic Activity in Mice," *Mol Cell Endocrinol.* 431:133-144, 2016.
Olsen et al., "Insights Into the Molecular Basis for Fibroblast Growth Factor Receptor Autoinhibition and Ligand-Binding Promiscuity," *Proc Natl Acad Sci. USA* 101:935-940, 2004.
Ono et al., "Novel Regulation of Fibroblast Growth Factor 2 (FGF20-Mediated Cell Growth by Polysialic Acid," *J Biol Chem.* 287:3710-3722, 2012.
Poa and Edgar, "Insulin Resistance Is Associated With Hypercortisolemia in Polynesian Patients Treated With Antipsychotic Medication," *Diabetes Care* 30:1425-1429, 2007.
Presta et al., "Structure-Function Relationship of Basic Fibroblast Growth Factor: Site-Directed Mutagenesis of a Putative Heparin-Binding and Receptor-Binding Region," *Biochem Biophys Res Commun.* 185:1098-1107, 1992.
Rafacho et al., "Glucocorticoid Treatment and Endocrine Pancreas Function: Implications for Glucose Homeostasis, Insulin Resistance and Diabetes," *J Endocrinol.* 223:R49-R62, 2014.
Razzaque, "The FGF23-Klotho Axis: Endocrine Regulation of Phosphate Homeostasis," *Nat Rev Endocrinol.* 5:611-619, 2009.
Schlessinger et al., "Crystal Structure of a Ternary FGF-FGFR-Heparin Complex Reveals a Dual Role for Heparin in FGFR Binding and Dimerization," *Mol. Cell* 6:743-750, 2000.
Thompson et al., "Energetic Characterization of the Basic Fibroblast Growth Factor-Heparin Interaction: Identification of the Heparin Binding Domains," *Biochem.* 33:3831-3840, 1994.
Wu et al., "C-Terminal Tail of FGF19 Determines Its Specificity Toward Klotho Co-Receptors," *J Biol Chem.* 283:33304-33309, 2008.
Wu et al., "Selective Activation of FGFR4 by an FGF19 Variant Does Not Improve Glucose Metabolism in ob/ob Mice," *Proc Natl Acad Sci. USA* 106:14379-14384, 2009.
Wu et al., "FGF19-Induced Hepatocyte Proliferation is Mediated Through FGFR4 Activation," *J Biol Chem.* 285:5165-5170, 2010.
Wu et al., "FGF19 Regulates Cell Proliferation, Glucose and Bile Acid Metabolism via FGFR4-Dependent and Independent Pathways," *PLoS One* 6:e17868, 2011.
Wu et al., "A Unique FGF23 With the Ability to Activate FGFR Signaling Through Both αKlotho and βKlotho," *J Mol Biol.* 418:82-89, 2012.
Yao et al., "Expression and Pharmacological Evaluation of Fusion Protein FGF21-L-Fc," *Acta Pharmaceutica Sinica* 46:787-792, 2011 (with English abstract).
Yie et al., "FGF21 N- and C-Termini Play Different Roles in Receptor Interaction and Activation," *FEBS Lett.* 583:19-24, 2009.
Zhang et al., "Receptor Specificity of the Fibroblast Growth Factor Family: The Complete Mammalian FGF Family," *J Biol Chem.* 281:15694-15700, 2006.
Storz et al., "Intellectual Property Issues Therapeutics, Vaccines and Molecular Diagnostics," Springer Science & Business Media, May 11, 2012 (115 pages).
Royce et al., "Incorporation of polymer microspheres within fibrin scaffolds for the controlled delivery of FGF-1," *J Biomater Sci Polymer Edn.* 15:1327-1336, 2004.
Xia et al.,"An S116R Phosphorylation Site Mutation in Human Fibroblast Growth Factor-1 Differentially Affects Mitogenic and Glucose-Lowering Activities," *J Pharm Sci.* 105:3507-3519, 2016.
Accession No. 1605206A, Sep. 14, 1996.
CN 201380039848.9 Office Action dated Jun. 8, 2017 (with English translation) (18 pages).
PCT/US2017/014049 International Search Report and Written Opinion dated Jun. 6, 2017, 24 pages.
PCTUS2017044678 International Search Report and Written Opinion dated Oct. 24, 2017 (18 pages).

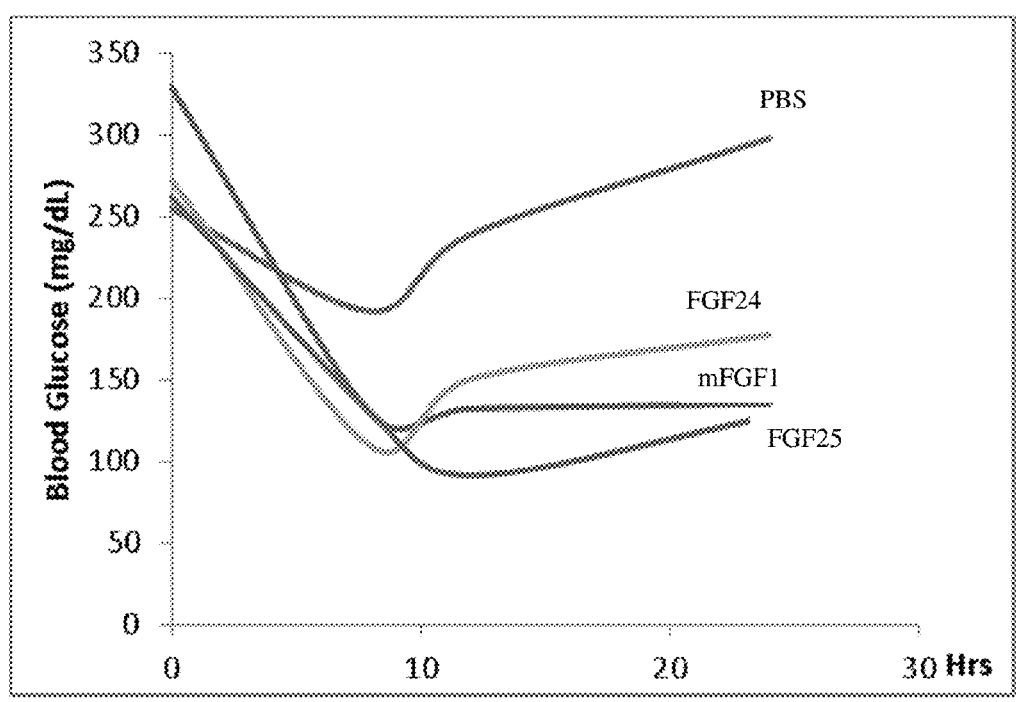

CHIMERIC FIBROBLAST GROWTH FACTOR (FGF) 2/FGF1 PEPTIDES AND METHODS OF USE

CROSS-REFERENCE TO RELATED APPLICATIONS

This is a continuation of International Application No. PCT/US2014/061593 filed Oct. 21, 2014, which was published in English under PCT Article 21(2), which in turn claims priority to U.S. Provisional Application No. 61/893,696 filed Oct. 21, 2013, herein incorporated by reference.

ACKNOWLEDGEMENT OF GOVERNMENT SUPPORT

This invention was made with government support under Grant Nos. DK057978, DK090962, HL088093, HL105278 and ES010337 awarded by The National Institutes of Health, National Human Genome Research Institute. The government has certain rights in the invention.

FIELD

This application provides FGF2/FGF1 chimeric proteins, and methods of their use, for example to treat a metabolic disease.

BACKGROUND

Type 2 diabetes and obesity are leading causes of mortality and are associated with the Western lifestyle, which is characterized by excessive nutritional intake and lack of exercise. A central player in the pathophysiology of these diseases is the nuclear hormone receptor (NHR) PPARγ, a lipid sensor and master regulator of adipogenesis. PPARγ is also the molecular target for the thiazolidinedione (TZD)-class of insulin sensitizers, which command a large share of the current oral anti-diabetic drug market. However, there are numerous side effects associated with the use of TZDs such as weight gain, liver toxicity, upper respiratory tract infection, headache, back pain, hyperglycemia, fatigue, sinusitis, diarrhea, hypoglycemia, mild to moderate edema, and anemia. Thus, the identification of new insulin sensitizers is needed.

SUMMARY

Provided herein are chimeric proteins that include an N-terminus coupled to a C-terminus, wherein the N-terminus comprises an N-terminal portion of fibroblast growth factor (FGF) 2 and the C-terminus comprises a portion of an FGF1 protein, wherein the chimeric protein comprises at least 95% sequence identity to SEQ ID NO: 9, 10, 11, 12 or 13, and retains the ability to reduce blood glucose levels in vivo. Such proteins are referred to herein as FGF2/FGF1 chimeric proteins, or FGF24 proteins. Thus, the chimeric protein can have at least 96%, at least 97%, at least 98% or at least 99% sequence identity to SEQ ID NO: 9, 10, 11, 12 or 13, and retain the ability to reduce blood glucose levels in vivo. In some examples, the FGF2/FGF1 chimeric protein includes or consists of SEQ ID NO: 9, 10, 11, 12 or 13.

Also provided are isolated nucleic acid molecules encoding the disclosed FGF2/FGF1 chimeric proteins, that is, a nucleic acid molecule encoding a protein having at least 95% sequence identity to SEQ ID NO: 9, 10, 11, 12 or 13. Vectors and cells that include such nucleic acid molecules are also provided.

Methods of using the disclosed FGF2/FGF1 chimeric proteins (or nucleic acid molecules encoding such) are provided. In some examples the methods include administering a therapeutically effective amount of a disclosed FGF2/FGF1 chimeric protein (or nucleic acid molecules encoding such) to reduce blood glucose in a mammal, such as a decrease of at least 5%, for example within 48 hours, within 24 hours, within 12 hours, within 8 hours, or within 6 hours. In some examples the methods include administering a therapeutically effective amount of a disclosed FGF2/FGF1 chimeric protein (or nucleic acid molecules encoding such) to treat a metabolic disease in a mammal, such as diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular diseases (e.g., hypertension), or combinations thereof. Also provided are methods of reducing fed and fasting blood glucose, improving insulin sensitivity and glucose tolerance, reducing systemic chronic inflammation, ameliorating hepatic steatosis in a mammal, or combinations thereof, by administering a therapeutically effective amount of a disclosed FGF2/FGF1 chimeric protein (or nucleic acid molecules encoding such). In some examples, use of the disclosed FGF2/FGF1 chimeric proteins (or nucleic acid molecules encoding such) results in one or more of: reduction in triglycerides, decrease in insulin resistance, reduction of hyperinsulinemia, increase in glucose tolerance, reduction of hyperglycemia, or combinations thereof, in a mammal.

The foregoing and other objects and features of the disclosure will become more apparent from the following detailed description, which proceeds with reference to the accompanying figures.

BRIEF DESCRIPTION OF THE DRAWING

FIG. 1 is a graph showing a decrease in blood glucose following administration of various peptides.

SEQUENCE LISTING

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOS: 1 and 2 provide exemplary human FGF2 nucleic acid and protein sequences, respectively. Source: GenBank Accession Nos: AB451450 and BAG70264, respectively. Heparan binding residues are amino acids 128-129, 134, 138, and 143-145 of SEQ ID NO: 2.

SEQ ID NOS: 3 and 4 provide an exemplary mouse FGF2 nucleic acid and protein sequences, respectively. Source: GenBank Accession Nos: NM_008006 and NP_032032.

SEQ ID NOS: 5 and 6 provide an exemplary human FGF1 nucleic acid and protein sequences, respectively. Source: GenBank Accession Nos: BC032697.1 and AAH32697.1.

SEQ ID NOS: 7 and 8 provide an exemplary mouse FGF1 nucleic acid and protein sequences, respectively. Source: GenBank Accession Nos: BC037601.1 and AAH37601.1.

SEQ ID NO: 9 provides an exemplary FGF2/FGF1 chimeric protein sequence (FGF24). FGF2 portion is amino acids 1-21, and the FGF1 portion is amino acids 22-158.

SEQ ID NO: 10 provides an exemplary FGF2/FGF1 chimeric protein sequence (FGF24.1). FGF2 portion is amino acids 1-21, and the FGF1 portion is amino acids 22-158.

SEQ ID NO: 11 provides an exemplary FGF2/FGF1 chimeric protein sequence (FGF24.2). FGF2 portion is amino acids 1-21, and the FGF1 portion is amino acids 22-158.

SEQ ID NO: 12 provides an exemplary FGF2/FGF1 chimeric protein sequence (FGF24 without the MAAGSITTL signal sequence). FGF2 portion is amino acids 1-12, and the FGF1 portion is amino acids 13-149.

SEQ ID NO: 13 provides an exemplary FGF2/FGF1 chimeric protein sequence (FGF24 with an N-terminal M instead of the MAAGSITTL signal sequence). FGF2 portion is amino acids 1-13, and the FGF1 portion is amino acids 14-150.

SEQ ID NO: 14 provides a coding sequence for FGF24 (SEQ ID NO: 9).

SEQ ID NO: 15 provides a coding sequence for FGF24.1 (SEQ ID NO: 10).

SEQ ID NO: 16 provides a coding sequence for FGF24.2 (SEQ ID NO: 11).

SEQ ID NOS: 17 and 18 provide a coding sequence and protein sequence for FGF25.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Oct. 21, 2013. All references and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject an agent, such as a chimeric protein, by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

C-terminal portion: A region of a protein sequence that includes a contiguous stretch of amino acids that begins at or near the C-terminal residue of the protein. A C-terminal portion of the protein can be defined by a contiguous stretch of amino acids (e.g., a number of amino acid residues).

Chimeric protein: A protein that includes at least a portion of the sequence of a full-length first protein (e.g., FGF2) and at least a portion of the sequence of a full-length second protein (e.g., FGF1), where the first and second proteins are different. A chimeric polypeptide also encompasses polypeptides that include two or more non-contiguous portions derived from the same polypeptide.

Diabetes Mellitus:

A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:

a. Fasting plasma glucose level≥7.0 mmol/l (126 mg/dl);
b. Plasma glucose≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%

Effective Amount or Therapeutically Effective Amount:

The amount of agent, such as a chimeric protein disclosed herein, that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as a diabetes (such as type II diabetes), for example by lowering blood glucose.

Fibroblast Growth Factor 1 (FGF1):

OMIM 13220. A protein that binds to the FGF receptor, and is also known as the acidic FGF. FGF1 sequences are publically available, for example from GenBank® sequence database (e.g., Accession Nos. NP_00791 and NP_034327 provide exemplary FGF1 protein sequences, while Accession Nos. NM_000800 and NM_010197 provide exemplary FGF1 nucleic acid sequences). Other examples are provided in SEQ ID NOS: 5-8. One of ordinary skill in the art can identify additional FGF1 nucleic acid and protein sequences, including FGF1 variants.

Fibroblast Growth Factor 2 (FGF2):

OMIM 134920. A protein that binds to the FGF receptor, and is also known as the basic FGF. FGF2 is present in basement membranes and in the subendothelial extracellular matrix of blood vessels. It stays membrane-bound as long as there is no signal peptide. FGF2 sequences are publically available, for example from GenBank® sequence database (e.g., Accession Nos. NP_001997 and NP_032032 provide exemplary FGF1 protein sequences, while Accession Nos. NM_002006 and NM_008006 provide exemplary FGF2 nucleic acid sequences). Other examples are provided in SEQ ID NOS: 1-4. One of ordinary skill in the art can identify additional FGF1 nucleic acid and protein sequences, including FGF2 variants.

Host Cells:

Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, host cells can be transgenic, in that they include nucleic acid molecules that have been introduced into the cell, such as a nucleic acid molecule encoding a chimeric protein disclosed herein.

Isolated:

An "isolated" biological component (such as a nucleic acid molecule or chimeric protein) has been substantially separated, produced apart from, or purified away from other biological components in the cell of the organism in which the component naturally occurs, such as other chromosomal and extrachromosomal DNA and RNA, and proteins. Nucleic acids molecules and chimeric proteins which have been "isolated" thus include nucleic acids and proteins purified by standard purification methods. The term also embraces nucleic acid molecules and chimeric proteins prepared by recombinant expression in a host cell as well as chemically synthesized nucleic acids. A purified cell, chimeric protein, or nucleic acid molecule can be at least 90%, at least 95%, at least 96%, at least 97%, at least 98%, or at least 99% pure.

Mammal:

This term includes both human and non-human mammals. Similarly, the term "subject" includes both human and veterinary subjects (such as cats, dogs, cows, and pigs).

Metabolic Disorder/Disease:

A disease or disorder that results from the disruption of the normal mammalian process of metabolism. Includes metabolic syndrome.

Examples include but are not limited to: (1) glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction; (2) dyslipidemias and their sequelae such as, for example, atherosclerosis, coronary artery disease, cerebrovascular disorders and the like; (3) other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; (4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; (5) disorders of cell cycle or cell differentiation processes such as adipose cell tumors, lipomatous carcinomas including, for example, liposarcomas, solid tumors, and neoplasms; (6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; (7) skin and dermatological disorders and/or disorders of wound healing processes, including erythematosquamous dermatoses; and (8) other disorders such as syndrome X, osteoarthritis, and acute respiratory distress syndrome. Other examples are provided in WO 2014/085365 (herein incorporated by reference).

In specific examples, the metabolic disease includes one or more of (such as at least 2 or at least 3 of): diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), and cardiovascular diseases (e.g., hypertension).

N-Terminal Portion:

A region of a protein sequence that includes a contiguous stretch of amino acids that begins at or near the N-terminal residue of the protein. An N-terminal portion of the protein can be defined by a contiguous stretch of amino acids (e.g., a number of amino acid residues).

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions (such as regions of FGF1 and FGF2), in the same reading frame.

Pharmaceutically Acceptable Carriers:

The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the chimeric proteins (or nucleic acid encoding such) herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter:

Ann array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant:

A recombinant nucleic acid molecule is one that has a sequence that is not naturally occurring or has a sequence that is made by an artificial combination of two otherwise separated segments of sequence (e.g., a FGF2/FGF1 chimera). This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule and expresses a recombinant protein.

Sequence Identity of Amino Acid Sequences:

The similarity between amino acid (or nucleic acid) sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the chimeric proteins disclosed herein are typically characterized by possession of at least about 95%, 96%, 97%, 98% or 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided. Thus, exemplary chimeric FGF2/FGF1 proteins have at least 80%, at least 85%, at least 90%, at least 92%, at least 95%, at least 96%, at least 97%, at least 98%, or at least 99% sequence identity to SEQ ID NO: 9, 10, 11, 12 or 13, and retain the ability to reduce blood glucose in a mammal, such as a mammal with a metabolic disease, such as diabetes.

Similarly, exemplary chimeric FGF2/FGF1 coding sequences have at least 70%, at least 80%, at least 85%, at least 90%, at least 92%, at least 95%, at least 96%, at least 97%, at least 98%, or at least 99% sequence identity to SEQ ID NO: 14, 15 or 16, and encode a protein with the ability to reduce blood glucose in a mammal, such as a mammal with a metabolic disease, such as diabetes.

Subject:

Any mammal, such as humans, non-human primates, pigs, sheep, cows, dogs, cats, veterinary subjects, rodents and the like which is to be the recipient of the particular treatment, such as treatment with a chimeric protein (or nucleic acid encoding such) provided herein. In two non-limiting examples, a subject is a human subject or a murine subject. In some examples, the subject has one or more metabolic diseases, such as diabetes (e.g., type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular disease (e.g., hypertension), or combinations thereof. In some examples, the subject has elevated blood glucose.

Transduced and Transformed:

A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA.

Transgene:

An exogenous gene supplied by a vector. In one example, a transgene includes an FGF2/FGF1 chimeric coding sequence.

Vector:

A nucleic acid molecule as introduced into a host cell, thereby producing a transformed host cell. A vector may include nucleic acid sequences that permit it to replicate in the host cell, such as an origin of replication. A vector may also include one or more FGF2/FGF1 chimeric coding sequences and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Overview

Provided herein are chimeric proteins that include an N-terminus coupled to a C-terminus, wherein the N-terminus comprises an N-terminal portion of fibroblast growth factor (FGF) 2 and the C-terminus comprises a portion of an FGF1 protein, wherein the chimeric protein comprises at least 95% sequence identity to SEQ ID NO: 9, 10, 11, 12 or 13 and has the ability to reduce blood glucose levels in vivo. Such proteins are referred to herein as FGF2/FGF1 chimeric proteins, or FGF24 proteins. Thus, the chimeric protein can have at least 96%, at least 97%, at least 98% or at least 99% sequence identity to SEQ ID NO: 9, 10, 11, 12 or 13, and retains the ability to reduce blood glucose levels in vivo. In some examples, the FGF2/FGF1 chimeric protein includes or consists of SEQ ID NO: 9, 10, 11, 12 or 13. The disclosure encompasses variants of the disclosed FGF2/FGF1 chimeric proteins, such as any of SEQ ID NOS: 9-13 having 1 to 8 conservative amino acid substitutions. Variants of SEQ ID NO: 9, 10, 11, 12 or 13 encompassed by this disclosure (such as those containing at least 95% sequence identity to these sequences, such as one containing 1 to 8 conservative amino acid substitutions or other variation), retain the ability to reduce blood glucose in a mammal, such as a mammal with a metabolic disease, such as diabetes. For example, administering a therapeutically effective amount of a disclosed mutated FGF2/FGF1 chimeric protein reduces blood glucose in a mammal, such as one with a metabolic disease, such as diabetes, for example a decrease of at least 5%, at least 10%, at least 25% or at least 50%.

Also provided are isolated nucleic acid molecules encoding the disclosed FGF2/FGF1 chimeric proteins, that is, a nucleic acid molecule encoding a protein having at least 95%, at least 96%, at least 97%, at least 98%, or at least 99% sequence identity to SEQ ID NO: 9, 10, 11, 12 or 13. Vectors and cells that include such nucleic acid molecules are also provided. For example, such nucleic acid molecules can be expressed in a host cell, such as a bacterium or yeast cell (e.g., *E. coli*), thereby permitting expression of the FGF2/FGF1 chimeric protein. The resulting FGF2/FGF1 chimeric protein can be purified from the cell.

Methods of using the disclosed FGF2/FGF1 chimeric proteins (or nucleic acid molecules encoding such) are provided. For example, such methods include administering a therapeutically effective amount of a disclosed FGF2/FGF1 chimeric protein (such as at least 0.5 mg/kg) (or nucleic acid molecules encoding such) to reduce blood glucose in a mammal, such as a decrease of at least 5%. In some examples, blood glucose is reduced by at least 5%, at least 10%, at least 20%, at least 25%, at least 30%, at least 40%, or at least 50% (such as 5 to 50%, 5 to 20%, 10 to 25% or 10 to 40%) in a subject in need of blood glucose reduction, such as one with one or more metabolic disorders, such as diabetes. In some examples, such reductions are achieved within 48 hours, within 24 hours, within 12 hours, within 8 hours, within 6 hours, within 4 hours, within 2 hours, within 1 hour, or within 30 minutes, such as 1 to 8 hours, 6 to 24 hours, or 8 to 24 hours.

In one example, the method is a method of reducing fed and fasting blood glucose, improving insulin sensitivity and glucose tolerance, reducing systemic chronic inflammation, ameliorating hepatic steatosis in a mammal, reducing triglycerides, decreasing insulin resistance, reducing hyperinsulinemia, increasing glucose tolerance, reducing hyperglycemia, or combinations thereof. Such a method can include administering a therapeutically effective amount of a disclosed FGF2/FGF1 chimeric protein (such as at least 0.5 mg/kg) (or nucleic acid molecules encoding such) to reduce fed and fasting blood glucose, improve insulin sensitivity and glucose tolerance, reduce systemic chronic inflammation, ameliorate hepatic steatosis in a mammal, or combinations thereof.

In one example, the method is a method of treating a metabolic disease (such as metabolic syndrome, diabetes, or obesity) in a mammal. Such a method can include administering a therapeutically effective amount of a disclosed FGF2/FGF1 chimeric protein (such as at least 0.5 mg/kg) (or nucleic acid molecules encoding such) to treat the metabolic disease.

In some examples, the mammal, such as a human, cat or dog, has diabetes. Methods of administration are routine, and can include subcutaneous, intraperitoneal, intramuscular, or intravenous injection.

In some examples, use of the FGF2/FGF1 chimeras disclosed herein does not lead to (or significantly reduces, such as a reduction of at least 20%, at least 50%, at least 75%, or at least 90%) the adverse side effects observed with thiazolidinediones (TZDs) therapeutic insulin sensitizers, including weight gain, increased liver steatosis and bone fractures (e.g., reduced affects on bone mineral density, trabecular bone architecture and cortical bone thickness).

Provided are methods of reducing fed and fasting blood glucose, improving insulin sensitivity and glucose tolerance, reducing systemic chronic inflammation, ameliorating hepatic steatosis, or combinations thereof, in a mammal. Such methods can include administering a therapeutically effective amount of a FGF2/FGF1 chimera disclosed herein, to the mammal, or a nucleic acid molecule encoding the chimera or a vector comprising the nucleic acid molecule, thereby reducing fed and fasting blood glucose, improving insulin sensitivity and glucose tolerance, reducing systemic chronic inflammation, ameliorating hepatic steatosis, reduce one or more non-HDL lipid levels, or combinations thereof, in a mammal. In some examples, the fed and fasting blood glucose is reduced in the treated subject by at least 10%, at least 20%, at least 30%, at least 50%, at least 75%, or at least 90% as compared to an absence of administration of the FGF2/FGF1 chimera. In some examples, insulin sensitivity and glucose tolerance is increased in the treated subject by at least 10%, at least 20%, at least 30%, at least 50%, at least 75%, or at least 90% as compared to an absence of administration of FGF2/FGF1 chimera. In some examples, systemic chronic inflammation is reduced in the treated subject by at least 10%, at least 20%, at least 30%, at least 50%, at least 75%, or at least 90% as compared to an absence of administration of FGF2/FGF1 chimera. In some examples, hepatic steatosis is reduced in the treated subject by at least 10%, at least 20%, at least 30%, at least 50%, at least 75%, or at least 90% as compared to an absence of administration of FGF2/FGF1 chimera. In some examples, one or more lipids (such as a non-HDL, for example IDL, LDL and/or VLDL) are reduced in the treated subject by at least 10%, at least 20%, at least 30%, at least 50%, at least 75%, or at least 90% as compared to an absence of administration of FGF2/FGF1 chimera. In some examples, triglyceride and or cholesterol levels are reduced with the FGF2/FGF1 chimera by at least 10%, at least 20%, at least 30%, at least 50%, at least 75%, or at least 90% as compared to an absence of administration of FGF2/FGF1 chimera. In some examples, combinations of these reductions are achieved.

FGF2/FGF1 Chimeric Proteins and Variants Thereof

The present disclosure provides chimeric proteins that include an N-terminal and a C-terminal portion, wherein the N-terminal portion includes an N-terminal portion of FGF2, while the C-terminal portion includes a portion of FGF1. In some examples, the chimeric FGF2/FGF1 protein is referred to as an FGF24 protein. FGFs are a family of growth factors, with members involved in angiogenesis, wound healing, embryonic development and various endocrine signaling pathways. The FGFs are heparan-binding proteins and interact with cell-surface-associated heparan sulfate proteoglycans. There are currently 22 FGF family members.

Exemplary FGF2/FGF1 chimeric proteins are provided in SEQ ID NOS: 9-13. One skilled in the art will recognize that minor variations can be made to these sequences, without adversely affecting the function of the protein. For example, variants of the FGF2/FGF1 chimeric proteins include those having at least 95%, at least 96%, at least 97%, at least 98%, or at least 99% sequence identity to SEQ ID NO: 9, 10, 11, 12 or 13, but retain the ability to decrease blood glucose in a mammal (such as a mammal with type II diabetes or other metabolic disorder), such as a decrease of at least 5%, at least 10%, at least 20%, at least 25%, or at least 50%. Thus, variants of SEQ ID NO: 9, 10, 11, 12 or 13 that retain at least 95% sequence identity and have the desired effect on blood glucose levels are of use in the disclosed methods.

Variant FGF2/FGF1 chimeric proteins (e.g., variants of SEQ ID NO: 9, 10, 11, 12 or 13) can contain a single insertion, a single deletion, a single substitution, 1-8 insertions, 1-8 deletions, 1-8 substitutions, or any combination thereof (e.g., single deletion together with 1-7 insertions). In some examples, the disclosure provides a variant of SEQ ID NO: 9, 10, 11, 12 or 13 having 1, 2, 3, 4, 5, 6, 7, or 8 amino acid changes. In one example, such polypeptides are produced by manipulating the nucleotide sequence encoding a polypeptide using standard procedures such as site-directed mutagenesis or PCR. In other example, such variants are chemically synthesized.

One type of modification includes the substitution of 1 to 8 amino acids for amino acid residues having a similar biochemical property, that is, a conservative substitution. Typically, conservative substitutions have little to no impact on the activity of a resulting peptide. For example, a conservative substitution is an amino acid substitution in SEQ ID NO: 9, 10, 11, 12 or 13 that does not substantially affect the ability of the peptide to decrease blood glucose in a mammal. An alanine scan can be used to identify which amino acid residues in SEQ ID NO: 9, 10, 11, 12 or 13 can tolerate an amino acid substitution. In one example, the activity of any of SEQ ID NO: 9, 10, 11, 12 or 13 is not altered by more than 25%, for example not more than 20%, for example not more than 10%, when an alanine, or other conservative amino acid, is substituted for 1-8 native amino acids. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Be for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed for any of SEQ ID NOS: 9-13 by analyzing the ability of the variant protein to decrease blood glucose in a mammal.

In some embodiments, the FGF2/FGF1 chimeric protein includes an FGF2 portion contiguously joined to an FGF1 portion. However, one skilled in the art will appreciate that in some examples, the FGF2 portion and the FGF1 portion are coupled by an intervening spacer, such as a peptide sequence of 1, 2, 3, 4, 5, 6, 7, 8, 9, 10, or more amino acid residues (such as alanine residues). Thus, any of SEQ ID NOs: 9, 10, 11, 12 and 13 can be modified to include such a spacer. For example, SEQ ID NO: 9 can be modified by introducing a spacer ([spacer]) as follows:

```
MAAGSITTL PALPEDGGSG AF [spacer] PPGNYK KPKLLYCSNG

GHFLRILPDG TVDGTRDRSD QHIQLQLSAE SVGEVYIKST

ETGQYLAMDT DGLLYGSQTP NEECLFLERL EENHYNTYIS

KKHAEKNWFVGLKKNGSCKR GPRTHYGQKA ILFLPLPVSSD
```

Isolation and purification of recombinantly expressed FGF2/FGF1 chimeric proteins can be carried out by conventional means including preparative chromatography and immunological separations. Once expressed, FGF2/FGF1 chimeric proteins can be purified according to standard procedures of the art, including ammonium sulfate precipitation, affinity columns, column chromatography, and the like (see, generally, R. Scopes, Protein Purification, Springer-Verlag, N.Y., 1982). Substantially pure compositions of at least about 90 to 95% homogeneity are disclosed herein, and 98 to 99% or more homogeneity can be used for pharmaceutical purposes.

In addition to recombinant methods, FGF2/FGF1 chimeric proteins disclosed herein can also be constructed in whole or in part using standard peptide synthesis. In one example, FGF2/FGF1 chimeric proteins are synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

FGF2/FGF1 Chimeric Nucleic Acid Molecules and Vectors

Nucleic acid molecules encoding a protein having at least 95%, at least 96%, at least 97%, at least 99% or at least 99% sequence identity to SEQ ID NO: 9, 10, 11, 12 or 13 can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same chimeric protein sequence. In one example, a chimeric FGF2/FGF1 nucleic acid sequence has at least 70%, at least 80%, at least 85%, at least 90%, at least 92%, at least 95%, at least 98%, or at least 99% sequence identity to SEQ ID NO: 14, 15 or 16.

Nucleic acid molecules include DNA, cDNA and RNA sequences which encode a FGF2/FGF1 chimeric peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W.H. 5 Freeman and Co., NY).

Codon preferences and codon usage tables for a particular species can be used to engineer isolated nucleic acid molecules encoding an FGF2/FGF1 chimeric protein (such as one encoding a protein having at least 95% sequence identity to any of SEQ ID NOS: 9-13) that take advantage of the codon usage preferences of that particular species. For example, the chimeric proteins disclosed herein can be designed to have codons that are preferentially used by a particular organism of interest.

A nucleic acid encoding an FGF2/FGF1 chimeric protein (such as one encoding a protein having at least 95%, at least 96%, at least 97%, at least 98%, or at least 99% sequence identity to SEQ ID NO: 9, 10, 11, 12 or 13) can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a nucleic acid molecule encoding a portion of an FGF2/FGF1 chimeric protein can be isolated by polymerase chain reaction of cDNA using primers based on the DNA sequence of FGF1 and FGF2, and the desired sequences ligated together to form the chimera. A wide variety of cloning and in vitro amplification methodologies are well known to persons skilled in the art. In addition, nucleic acids encoding sequences encoding an FGF2/FGF1 chimeric protein (such as one encoding a protein having at least 95%, at least 96%, at least 97%, at least 98%, or at least 99% sequence identity to SEQ ID NO: 9, 10, 11, 12 or 13) can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding an FGF2/FGF1 chimeric protein (such as one encoding a protein having at least 95% sequence identity to SEQ ID NO: 9, 10, 11, 12 or 13) can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, an FGF2/FGF1 chimeric protein (such as one encoding a protein having at least 95% sequence identity to SEQ ID NO: 9, 10, 11, 12 or 13) is prepared by inserting the cDNA which encodes the chimeric protein into a vector. The insertion can be made so that the individual portion of the chimeric protein (such as the N- and C-terminal portions) are read in frame so that one continuous FGF2/FGF1 chimeric protein is produced.

The FGF2/FGF1 chimeric protein nucleic acid coding sequence (such as one encoding a protein having at least 95% sequence identity to SEQ ID NO: 9, 10, 11, 12 or 13) can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect, plant and mammalian organisms. Methods of expressing DNA sequences having eukaryotic or viral sequences in prokaryotes are well known in the art. Biologically functional viral and plasmid DNA vectors capable of expression and replication in a host are known in the art. The vector can encode a selectable marker, such as a thymidine kinase gene.

Nucleic acid sequences encoding an FGF2/FGF1 chimeric protein (such as one encoding a protein having at least 95%, at least 96%, at least 97%, at least 98%, or at least 99% sequence identity to SEQ ID NO: 9, 10, 11, 12 or 13) can be operatively linked to expression control sequences. An expression control sequence operatively linked to an FGF2/FGF1 chimeric protein coding sequence is ligated such that expression of the chimeric protein coding sequence is achieved under conditions compatible with the expression control sequences. The expression control sequences include, but are not limited to appropriate promoters, enhancers, transcription terminators, a start codon (i.e., ATG) in front of an FGF2/FGF1 chimeric protein-encoding gene, splicing signal for introns, maintenance of the correct reading frame of that gene to permit proper translation of mRNA, and stop codons.

In one embodiment, vectors are used for expression in yeast such as *S. cerevisiae*, *P. pastoris*, or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2φ or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on K. lactis are known, such as pKLAC1. Thus, in one example, after amplification in bacteria, plasmids can be introduced into the corresponding yeast auxotrophs by methods similar to bacterial transformation. The nucleic acid molecules encoding an FGF2/FGF1 chimeric protein (such as one encoding a protein having at least 95%, at least 96%, at least 97%, at least 98%, or at least 99% sequence identity to SEQ ID NO: 9, 10, 11, 12 or 13) can also be designed to express in insect cells.

An FGF2/FGF1 chimeric protein (such as one having at least 95%, at least 96%, at least 97%, at least 98%, or at least 99% sequence identity to SEQ ID NO: 9, 10, 11, 12 or 13) can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast cell lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared that encode an FGF2/FGF1 chimeric protein (such as one encoding a protein having at least 95%, at least 96%, at least 97%, at least 98%, or at least 99% sequence identity to SEQ ID NO: 9, 10, 11, 12 or 13). Exemplary viral vectors include polyoma, SV40, adenovirus, vaccinia virus, adeno-associated virus, herpes viruses including HSV and EBV, Sindbis viruses, alphaviruses and retroviruses of avian, murine, and human origin. Baculovirus (Autographa californica multinuclear polyhedrosis virus; AcMNPV) vectors are also known in the art, and may be obtained from commercial sources. Other suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

Viral vectors that encode an FGF2/FGF1 chimeric protein (such as one encoding a protein having at least 95%, at least 96%, at least 97%, at least 98%, or at least 99% sequence identity to SEQ ID NO: 9, 10, 11, 12 or 13) can include at least one expression control element operationally linked to the nucleic acid sequence encoding the FGF2/FGF1 chimeric protein. The expression control elements are inserted in the vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the FGF2/FGF1 chimeric protein in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the FGF2/FGF1 chimeric protein (such as one encoding a protein having at least 95%, at least 96%, at least 97%, at least 98%, or at least 99% sequence identity to a SEQ ID NO: 9, 10, 11, 12 or 13) are known. Such techniques involve, for example, homologous recombination between the viral DNA sequences flanking the DNA sequence in a donor plasmid and homologous sequences present in the parental virus. The vector can be constructed for example by steps known in the art, such as by using a unique restriction endonuclease site that is naturally present or artificially inserted in the parental viral vector to insert the heterologous DNA.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an FGF2/FGF1 chimeric protein (such as one encoding a protein having at least 95%, at least 96%, at least 97%, at least 98%, or at least 99% sequence identity to SEQ ID NO: 9, 10, 11, 12 or 13), and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing FGF2/FGF1 chimeric proteins in cells including higher eukaryotic cells such as the COS, CHO, HeLa and myeloma cell lines.

Cells Expressing FGF2/FGF1 Chimeric Proteins

A nucleic acid molecule encoding an FGF2/FGF1 chimeric protein disclosed herein can be used to transform cells and make transformed cells. Thus, cells expressing an FGF2/FGF1 chimeric protein (such as a protein having at least 95%, at least 96%, at least 97%, at least 98%, or at least 99% sequence identity to SEQ ID NO: 9, 10, 11, 12 or 13) are disclosed. Cells expressing an FGF2/FGF1 chimeric protein disclosed herein can be eukaryotic or prokaryotic. Examples of such cells include, but are not limited to bacteria, archea, plant, fungal, yeast, insect, and mammalian cells, such as *Lactobacillus, Lactococcus, Bacillus* (such as *B. subtilis*), *Escherichia* (such as *E. coli*), *Clostridium, Saccharomyces* or *Pichia* (such as *S. cerevisiae* or *P. pastoris*), *Kluyveromyces lactis, Salmonella typhimurium*, SF9 cells, C129 cells, 293 cells, *Neurospora*, and immortalized mammalian myeloid and lymphoid cell lines.

Cells expressing an FGF2/FGF1 chimeric protein are transformed or recombinant cells. Such cells can include at least one exogenous nucleic acid molecule that encodes an FGF2/FGF1 chimeric protein, for example a sequence encoding a protein having at least 95%, at least 96%, at least 97%, at least 98%, or at least 99% sequence identity to SEQ ID NO: 9, 10, 11, 12 or 13. It is understood that all progeny may not be identical to the parental cell since there may be mutations that occur during replication. Methods of stable transfer, meaning that the foreign DNA is continuously maintained in the host cell, are known in the art.

Transformation of a host cell with recombinant DNA may be carried out by conventional techniques as are well known. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. Techniques for the transformation of yeast cells, such as polyethylene glycol transformation, protoplast transformation and gene guns are also known in the art.

Pharmaceutical Compositions that Include FGF2/FGF1 Chimeras

Pharmaceutical compositions that include an FGF2/FGF1 chimeric protein (such as a protein having at least 95%, at least 96%, at least 97%, at least 98%, or at least 99% sequence identity to SEQ ID NO: 9, 10, 11, 12 or 13) or a nucleic acid encoding these proteins, can be formulated with an appropriate pharmaceutically acceptable carrier, depending upon the particular mode of administration chosen.

In some embodiments, the pharmaceutical composition consists essentially of an FGF2/FGF1 chimeric protein (such as a protein having at least 95%, at least 96%, at least 97%, at least 98%, or at least 99% sequence identity to any of SEQ ID NOS: 9-13) (or a nucleic acid encoding such a protein) and a pharmaceutically acceptable carrier. In these embodiments, additional therapeutically effective agents are not included in the compositions.

In other embodiments, the pharmaceutical composition includes an FGF2/FGF1 chimeric protein (such as a protein having at least 95%, at least 96%, at least 97%, at least 98%, or at least 99% sequence identity to SEQ ID NO: 9, 10, 11, 12 or 13) (or a nucleic acid encoding such a protein) and a pharmaceutically acceptable carrier. Additional therapeutic agents, such as agents for the treatment of diabetes, can be included. Thus, the pharmaceutical compositions can include a therapeutically effective amount of another agent. Examples of such agents include, without limitation, anti-apoptotic substances such as the Nemo-Binding Domain and compounds that induce proliferation such as cyclin dependent kinase (CDK)-6, CDK-4 and cyclin D1. Other active agents can be utilized, such as antidiabetic agents for example, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMG-CoA) reductase inhibitors (such as a statin), insulin and insulin analogues, GLP-1 and GLP-1 analogues (e.g. exendin-4) or amylin. Additional examples include immunomodulatory factors such as anti-CD3 mAb, growth factors such as HGF, VEGF, PDGF, lactogens, and PTHrP. In some examples, the pharmaceutical compositions containing an FGF2/FGF1 chimeric protein can further include a therapeutically effective amount of other FGFs, such as FGF21, FGF19, or both, heparin, or combinations thereof.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, an FGF2/FGF1 chimeric protein (such as a protein having at least 95%, at least 96%, at least 97%, at least 98%, or at least 99% sequence identity to SEQ ID NO: 9, 10, 11, 12 or 13) is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Patent Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other embodiments, an FGF2/FGF1 chimeric protein (such as a protein having at least 95%, at least 96%, at least 97%, at least 98%, or at least 99% sequence identity to SEQ ID NO: 9, 10, 11, 12 or 13) is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006. With regard to the administration of nucleic acids, one approach to administration of nucleic acids is direct treatment with plasmid DNA, such as with a mammalian expression plasmid. As described above, the nucleotide sequence encoding an FGF2/FGF1 chimeric protein (such as a protein having at least 95%, at least 96%, at least 97%, at least 98%, or at least 99% sequence identity to SEQ ID NO: 9, 10, 11, 12 or 13) can be placed under the control of a promoter to increase expression of the protein.

Many types of release delivery systems are available and known. Examples include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an FGF2/FGF1 chimeric protein (such as a protein having at least 95% sequence identity to any of SEQ ID NOS: 9-13), or polynucleotide encoding this chimeric protein, is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as diabetes. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with nucleic acids (see U.S. Pat. No. 6,218,371). For use in vivo, nucleic acids and peptides are preferably relatively resistant to degradation (such as via endo- and exo-nucleases). Thus, modifications of the disclosed FGF2/FGF1 chimeric proteins, such as the inclusion of a C-terminal amide, can be used.

The dosage form of the pharmaceutical composition can be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions that include an FGF2/FGF1 chimeric protein (such as a protein having at least 95%, at least 96%, at least 97%, at least 98%, or at least 99% sequence identity to SEQ ID NO: 9, 10, 11, 12 or 13) can be formulated in unit dosage form, suitable for individual administration of precise dosages. In one non-limiting example, a unit dosage contains from about 1 mg to about 1 g of an FGF2/FGF1 chimeric protein (such as a protein having at least 95%, at least 96%, at least 97%, at least 98%, or at least 99% sequence identity to any SEQ ID NO: 9, 10, 11, 12 or 13), such as about 10 mg to about 100 mg, about 50 mg to about 500 mg, about 100 mg to about 900 mg, about 250 mg to about 750 mg, or about 400 mg to about 600 mg. In other examples, a therapeutically effective amount of an FGF2/FGF1 chimeric protein (such as a protein having at least 95%, at least 96%, at least 97%, at least 98%, or at least 99% sequence identity to SEQ ID NO: 9, 10, 11, 12 or 13) is about 0.01 mg/kg to about 50 mg/kg, for example, about 0.5 mg/kg to about 25 mg/kg or about 1 mg/kg to about 10 mg/kg. In other examples, a therapeutically effective amount of an FGF2/FGF1 chimeric protein (such as a protein having at least 95% sequence identity to SEQ ID NO: 9, 10, 11, 12 or 13) is about 1 mg/kg to about 5 mg/kg, for example about 2 mg/kg. In a particular example, a therapeutically effective amount of an FGF2/FGF1 chimeric protein (such as a protein having at least 95%, at least 96%, at least 97%, at least 98%, or at least 99% sequence identity to SEQ ID NO: 9, 10, 11, 12 or 13) includes about 1 mg/kg to about 10 mg/kg, such as about 2 mg/kg.

Treatment Using FGF2/FGF1 Chimeras

The disclosed FGF2/FGF1 chimeric proteins (such as a protein having at least 95%, at least 96%, at least 97%, at least 98%, or at least 99% sequence identity to SEQ ID NO: 9, 10, 11, 12 or 13), or nucleic acids encoding such proteins, can be administered to a subject, for example to treat a metabolic disease, for example by reducing fed and fasting blood glucose, improving insulin sensitivity and glucose tolerance, reducing systemic chronic inflammation, ameliorating hepatic steatosis in a mammal, or combinations thereof.

The compositions of this disclosure that include an FGF2/FGF1 chimeric protein (such as a protein having at least 95%, at least 96%, at least 97%, at least 98%, or at least 99% sequence identity to SEQ ID NO: 9, 10, 11, 12 or 13) (or nucleic acids encoding these molecules) can be administered to humans or other animals by any means, including orally, intravenously, intramuscularly, intraperitoneally, intranasally, intradermally, intrathecally, subcutaneously, via inhalation or via suppository. In one non-limiting example, the composition is administered via injection. In some examples, site-specific administration of the composition can be used, for example by administering an FGF2/FGF1 chimeric protein (such as a protein having at least 95%, at least 96%, at least 97%, at least 98%, or at least 99% sequence identity to SEQ ID NO: 9, 10, 11, 12 or 13) (or a nucleic acid encoding these molecules) to pancreas tissue (for example by using a pump, or by implantation of a slow release form at the site of the pancreas). The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of an FGF2/FGF1 chimeric protein (such as a protein having at least 95% sequence identity to SEQ ID NO: 9, 10, 11, 12 or 13) can be administered in a single dose, twice daily, weekly, or in several doses, for example daily, or during a course of treatment. In a particular non-limiting example, treatment involves once daily dose or twice daily dose.

The amount of FGF2/FGF1 chimeric protein (such as a protein having at least 95%, at least 96%, at least 97%, at least 98%, or at least 99% sequence identity to SEQ ID NO: 9, 10, 11, 12 or 13) administered can be dependent on the subject being treated, the severity of the affliction, and the manner of administration, and is best left to the judgment of the prescribing clinician. Within these bounds, the formulation to be administered will contain a quantity of the FGF2/FGF1 chimeric protein in amounts effective to achieve the desired effect in the subject being treated. A therapeutically effective amount of FGF2/FGF1 chimeric protein (such as a protein having at least 95%, at least 96%, at least 97%, at least 98%, or at least 99% sequence identity to SEQ ID NO: 9, 10, 11, 12 or 13 can be the amount of the chimeric protein, or a nucleic acid encoding these molecules that is necessary to treat diabetes or reduce blood glucose levels (for example a reduction of at least 20%).

When a viral vector is utilized for administration of an nucleic acid encoding an FGF2/FGF1 chimeric protein (such as a protein having at least 95%, at least 96%, at least 97%, at least 98%, or at least 99% sequence identity to SEQ ID NO: 9, 10, 11, 12 or 13), the recipient can receive a dosage of each recombinant virus in the composition in the range of from about $10^5$ to about $10^{10}$ plaque forming units/mg mammal, although a lower or higher dose can be administered. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the pancreases in a pharmaceutically acceptable carrier. Generally, the quantity of recombinant viral vector, carrying the nucleic acid sequence of the FGF2/FGF1 chimeric protein to be administered (such as a protein having at least 95%, at least 96%, at least 97%, at least 98%, or at least 99% sequence identity to SEQ ID NO: 9, 10, 11, 12 or 13) is based on the titer of virus particles. An exemplary range to be administered is $10^5$ to $10^{10}$ virus particles per mammal, such as a human.

In some examples, the FGF2/FGF1 chimeric protein (such as a protein having at least 95%, at least 96%, at least 97%, at least 98%, or at least 99% sequence identity to SEQ ID NO: 9, 10, 11, 12 or 13), or a nucleic acid encoding the FGF2/FGF1 chimeric protein, is administered in combination (such as sequentially or simultaneously or contemporaneously) with one or more other agents, such as those useful in the treatment of diabetes or insulin resistance.

Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in *Diabetes Care,* 22(4):623-634. One class of anti-diabetic agents of use is the sulfonylureas, which are believed to increase secretion of insulin, decrease hepatic glucogenesis, and increase insulin receptor sensitivity. Another class of anti-diabetic agents of use the biguanide antihyperglycemics, which decrease hepatic glucose production and intestinal absorption, and increase peripheral glucose uptake and utilization, without inducing hyperinsulinemia.

In some examples, the FGF2/FGF1 chimeric protein (such as a protein having at least 95%, at least 96%, at least 97%, at least 98%, or at least 99% sequence identity to SEQ ID NO: 9, 10, 11, 12 or 13) can be administered in combination with effective doses of anti-diabetic agents (such as biguanides, thiazolidinediones, or incretins) and/or lipid lowering compounds (such as statins or fibrates). The term "administration in combination" or "co-administration" refers to both concurrent and sequential administration of the active agents. Administration of the FGF2/FGF1 chimeric protein (such as a protein having at least 95%, at least 96%, at least 97%, at least 98%, or at least 99% sequence identity to SEQ ID NO: 9, 10, 11, 12 or 13) or a nucleic acid encoding such a chimeric protein, may also be in combination with lifestyle modifications, such as increased physical activity, low fat diet, low sugar diet, and smoking cessation. Additional agents of use include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, metformin, sulphonylureas (e.g., glibenclamide, tolbutamide, glimepiride), nateglinide, repaglinide, thiazolidinediones (e.g., pioglitazone, rosiglitazone, rivoglitazone, or troglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g., exendin-4) or amylin. In some embodiments the agent is an immunomodulatory factor such as anti-CD3 mAb, growth factors such as HGF, vascular endothelial growth factor (VEGF), platelet derived growth factor (PDGF), lactogens, or parathyroid hormone related protein (PTHrP). In one example, the FGF2/FGF1 chimeric protein is administered in combination with a therapeutically effective amount of another FGF, such as FGF21, FGF19, or both, heparin, or combinations thereof.

In some embodiments, methods are provided for treating diabetes or pre-diabetes in a subject by administering a therapeutically effective amount of a composition including an FGF2/FGF1 chimeric protein (such as a protein having at least 95%, at least 96%, at least 97%, at least 98%, or at least 99% sequence identity to SEQ ID NO: 9, 10, 11, 12 or 13), or a nucleic acid encoding the chimeric protein, to the subject. The subject can have diabetes type I or diabetes type II. The subject can be any mammalian subject, including human subjects. The subject can be a child or an adult. The subject can also be administered insulin. The method can include measuring blood glucose levels.

In some examples, the method includes selecting a subject with diabetes, such as type I or type II diabetes, or a subject at risk for diabetes, such as a subject with pre-diabetes. These subjects can be selected for treatment with the disclosed FGF2/FGF1 chimeric proteins (such as a protein having at least 95%, at least 96%, at least 97%, at least 98%, or at least 99% sequence identity to SEQ ID NO: 9, 10, 11, 12 or 13) or nucleic acid molecules encoding such.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in Standards of Medical Care in Diabetes—2010 (American Diabetes Association, *Diabetes Care* 33:S11-61, 2010).

In some examples, the subject treated with the disclosed compositions and methods has HbA1C of greater than 6.5% or greater than 7%.

In some examples, treating diabetes includes one or more of increasing glucose tolerance, decreasing insulin resistance (for example, decreasing plasma glucose levels, decreasing plasma insulin levels, or a combination thereof), decreasing serum triglycerides, decreasing free fatty acid levels, and decreasing HbA1c levels in the subject. In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of a FGF2/FGF1 chimeric protein (such as a protein having at least 95%, at least 96%, at least 97%, at least 98%, or at least 99% sequence identity to SEQ ID NO: 9, 10, 11, 12 or 13), or nucleic acid molecule encoding such, treats a metabolic disease, such as diabetes (such as type II diabetes) or pre-diabetes, by decreasing of HbA1C, such as a reduction of at least 0.5%, at least 1%, or at least 1.5%, such as a decrease of 0.5% to 0.8%, 0.5% to 1%, 1 to 1.5% or 0.5% to 2%. In some examples the target for HbA1C is less than about 6.5%, such as about 4-6%, 4-6.4%, or 4-6.2%. In some such target levels are achieved within about 26 weeks, within about 40 weeks, or within about 52 weeks. Methods of measuring HbA1C are routine, and the disclosure is not limited to particular methods. Exemplary methods include HPLC, immunoassays, and boronate affinity chromatography.

In some examples, administration of a FGF2/FGF1 chimeric protein (such as a protein having at least 95%, at least 96%, at least 97%, at least 98%, or at least 99% sequence identity to SEQ ID NO: 9, 10, 11, 12 or 13), or nucleic acid molecule encoding such, treats diabetes or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, at least 15%, at least 20%, at least 25%, at least 30%, at least 35%, or more) as compared with a control (such as no administration of any of insulin, a FGF2/FGF1 chimeric protein (such as a protein having at least 95%, at least 96%, at least 97%, at least 98%, or at least 99% sequence identity to SEQ ID NO: 9, 10, 11, 12 or 13), or a nucleic acid molecule encoding such). In particular examples, a decrease in blood glucose level is determined relative to the starting blood glucose level of the subject (for example, prior to treatment with a FGF2/FGF1 chimeric protein (such as a protein having at least 95%, at least 96%, at least 97%, at least 98%, or at least 99% sequence identity to SEQ ID NO: 9, 10, 11, 12 or 13), or nucleic acid molecule encoding such). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In other embodiments, the disclosed methods include comparing one or more indicator of diabetes (such as glucose tolerance, triglyceride levels, free fatty acid levels, or HbA1c levels) to a control (such as no administration of any of insulin, a FGF2/FGF1 chimeric protein (such as a protein having at least 95%, at least 96%, at least 97%, at least 98%, or at least 99% sequence identity to SEQ ID NO: 9, 10, 11, 12 or 13), or a nucleic acid molecule encoding such), wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

Example 1

Preparation of Chimeric Proteins

FGF2/FGF1 chimeric proteins can be made using known methods (e.g., see Xia et al., *PLoS One.* 7(11):e48210, 2012). A non-limiting example is provided here.

A nucleic acid sequence encoding a FGF2/FGF1 chimeric sequence (SEQ ID NO: 9) can be fused downstream of an enterokinase (EK) recognition sequence (Asp$_4$Lys) preceded by a flexible 20 amino acid linker (derived from the S-tag sequence of pBAC-3) and an N-terminal (His)$_6$ tag. The resulting expressed fusion protein utilizes the (His)$_6$ tag for efficient purification and can be subsequently processed by EK digestion to yield the FGF2/FGF1 chimeric protein.

The FGF2/FGF1 chimeric protein can be expressed from an *E. coli* host after induction with isopropyl-β-D-thiogalactoside. The expressed protein can be purified utilizing sequential column chromatography on Ni-nitrilotriacetic acid (NTA) affinity resin followed by ToyoPearl HW-40S size exclusion chromatography. The purified protein can be digested with EK to remove the N-terminal (His)$_6$ tag, 20 amino acid linker, and (Asp$_4$Lys) EK recognition sequence. A subsequent second Ni-NTA chromatographic step can be utilized to remove the released N-terminal FGF2/FGF1 chimeric protein (along with any uncleaved fusion protein). Final purification can be performed using HiLoad Superdex 75 size exclusion chromatography equilibrated to 50 mM Na$_2$PO$_4$, 100 mM NaCl, 10 mM (NH$_4$)$_2$SO$_4$, 0.1 mM ethylenediaminetetraacetic acid (EDTA), 5 mM L-Methionine, pH at 6.5 ("PBX" buffer); L-Methionine can be included in PBX buffer to limit oxidization of reactive thiols and other potential oxidative degradation.

In some examples, the enterokinase is not used, and instead, an FGF2/FGF1 chimeric protein (such as one that includes an N-terminal methionine) can be made and purified using heparin affinity chromatography.

For storage and use, the purified chimeric protein can be sterile filtered through a 0.22 micron filter, purged with N$_2$, snap frozen in dry ice and stored at −80° C. prior to use. The purity of the chimeric protein can be assessed by both Coomassie Brilliant Blue and Silver Stain Plus (BIO-RAD Laboratories, Inc., Hercules Calif.) stained sodium dodecyl-sulfate polyacrylamide gel electrophoresis (SDS PAGE). FGF2/FGF1 chimeric proteins can be prepared in the absence of heparin. Prior to IV bolus, heparin, or PBS, can be added to the protein.

Example 2

FGF1/FGF2 Chimera Reduces Blood Glucose in Ob/Ob Mice

Ob/ob mice about 6 month's in age were used. Mice were fed ad lib throughout the procedure. Blood glucose levels were measured from tail bleeds using a novaMax glucometer (Nova diabetes care, Inc., USA).

Mice were injected subcutaneously at 0.5 mg/kg with (a) PBS; negative control; (b) mouse FGF1; positive control (SEQ ID NO: 8 but lacking first 15 a.a. MAEGEIT-TFAALTER and with an added M at N terminus); (c) FGF24 (SEQ ID NO: 9) or (d) FGF25 (SEQ ID NO: 18; which is human FGF1 (SEQ ID NO: 6) with codon usage changes to improve expression in bacteria).

As shown in FIG. 1 and Tables 1 and 2, a single bolus of FGF24 and FGF25 can reduce blood glucose levels in obese and diabetic ob/ob mouse over a period of days.

TABLE 1

Glucose Trends

| | | time | | | |
|---|---|---|---|---|---|
| ID | treatment | 3/12 2AM 0 | 3/12 10AM 8 | 3/12 2PM 12 | 3/13 2AM 24 |
| 7-O | PBS | 245 | 191 | 236 | 226 |
| 7-R | PBS | 265 | 193 | 242 | 370 |
| 1-O | mFGF1 | 371 | 108 | 143 | 130 |
| 1-R | mFGF1 | 288 | 151 | 122 | 141 |
| 8-O | FGF24 | 270 | 113 | 131 | 225 |
| 8-R | FGF24 | 275 | 106 | 170 | 130 |
| 9-O | FGF25 | 315 | 126 | 88 | 158 |
| 9-R | FGF25 | 209 | 134 | 95 | 97 |

TABLE 2

Averages for each group (n = 2 per group)

| | time | | | |
|---|---|---|---|---|
| | 3/12 2AM | 3/12 10AM | 3/12 2PM | 3/13 2AM |
| | hrs post-inj | | | |
| | 0 | 8 | 12 | 24 |
| PBS | 255 | 192 | 239 | 298 |
| mFGF1 | 329.5 | 129.5 | 132.5 | 135.5 |
| FGF24 | 272.5 | 109.5 | 150.5 | 177.5 |
| FGF25 | 262 | 130 | 91.5 | 127.5 |

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of reducing blood glucose in a mammal, comprising:
   administering a therapeutically effective amount of a chimeric protein to the mammal, thereby reducing the blood glucose, wherein the chimeric protein comprises an N-terminus coupled to a C-terminus, wherein the N-terminus comprises an N-terminal portion of an fibroblast growth factor (FGF) 2 protein and the C-terminus comprises a portion of an FGF1 protein, wherein the chimeric protein comprises at least 95% sequence identity to SEQ ID NO: 9.

2. The method of claim 1, wherein the therapeutically effective amount of the chimeric protein is at least 0.5 mg/kg.

3. The method of claim 1, wherein the administering is subcutaneous, intraperitoneal, intramuscular, or intravenous.

4. The method of claim 1, wherein the mammal is a cat or dog.

5. The method of claim 1, wherein the mammal is a human.

6. The method of claim 1, wherein the chimeric protein is administered in combination with an additional therapeutic compound.

7. The method of claim 6, wherein the additional therapeutic compound is an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

8. The method of claim 7, wherein the PPAR-gamma agonist is a thiazolidinedione (TZD), aleglitazar, farglitazar, muraglitazar, or tesaglitazar.

9. The method of claim 8, wherein the TZD is pioglitazone, rosiglitazone, rivoglitazone, or troglitazone.

10. The method of claim 1, wherein the chimeric protein comprises at least 96% sequence identity to SEQ ID NO: 9.

11. The method of claim 1, wherein the chimeric protein comprises at least 97% sequence identity to SEQ ID NO: 9.

12. The method of claim 1, wherein the chimeric protein comprises at least 98% sequence identity to SEQ ID NO: 9.

13. The method of claim 1, wherein the chimeric protein comprises at least 99% sequence identity to SEQ ID NO: 9.

14. The method of claim 1, wherein the chimeric protein comprises SEQ ID NO: 9.

15. The method of claim 1, wherein the chimeric protein consists of SEQ ID NO: 9.

16. The method of claim 1, wherein the chimeric protein comprises 1 to 8 conservative amino acid substitutions.

17. A method of reducing fed and fasting blood glucose, improving insulin sensitivity and glucose tolerance, reducing systemic chronic inflammation, ameliorating hepatic steatosis in a mammal, or combinations thereof, comprising:
administering a therapeutically effective amount of a chimeric protein to the mammal, thereby reducing fed and fasting blood glucose, improving insulin sensitivity and glucose tolerance, reducing systemic chronic inflammation, ameliorating hepatic steatosis in a mammal, or combinations thereof, wherein the chimeric protein comprises an N-terminus coupled to a C-terminus, wherein the N-terminus comprises an N-terminal portion of an fibroblast growth factor (FGF) 2 protein and the C-terminus comprises a portion of an FGF1 protein, wherein the chimeric protein comprises at least 95% sequence identity to SEQ ID NO: 9.

18. The method of claim 17, wherein the therapeutically effective amount of the chimeric protein is at least 0.5 mg/kg.

19. The method of claim 17, wherein the administering is subcutaneous, intraperitoneal, intramuscular, or intravenous.

20. The method of claim 17, wherein the mammal is a cat or dog.

21. The method of claim 17, wherein the mammal is a human.

22. The method of claim 17, wherein the chimeric protein is administered in combination with an additional therapeutic compound.

23. The method of claim 17, wherein the additional therapeutic compound is an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

24. The method of claim 23, wherein the PPAR-gamma agonist is a thiazolidinedione (TZD), aleglitazar, farglitazar, muraglitazar, or tesaglitazar.

25. The method of claim 24, wherein the TZD is pioglitazone, rosiglitazone, rivoglitazone, or troglitazone.

26. The method of claim 17, wherein the chimeric protein comprises at least 96% sequence identity to SEQ ID NO: 9.

27. The method of claim 17, wherein the chimeric protein comprises at least 97% sequence identity to SEQ ID NO: 9.

28. The method of claim 17, wherein the chimeric protein comprises at least 98% sequence identity to SEQ ID NO: 9.

29. The method of claim 17, wherein the chimeric protein comprises at least 99% sequence identity to SEQ ID NO: 9.

30. The method of claim 17, wherein the chimeric protein comprises SEQ ID NO: 9.

31. The method of claim 17, wherein the chimeric protein consists of SEQ ID NO: 9.

32. The method of claim 17, wherein the chimeric protein comprises 1 to 8 conservative amino acid substitutions.

* * * * *

SEQUENCE LISTING

<160> NUMBER OF SEQ ID NOS: 18

<210> SEQ ID NO 1
<211> LENGTH: 465
<212> TYPE: DNA
<213> ORGANISM: Homo sapiens -continued

```
<220> FEATURE:
<221> NAME/KEY: CDS
<222> LOCATION: (1)..(465)

<400> SEQUENCE: 1 atg gca gcc ggg agc atc acc acg ctg ccc gcc ttg ccc gag gat ggc      48
Met Ala Ala Gly Ser Ile Thr Thr Leu Pro Ala Leu Pro Glu Asp Gly
1               5                   10                  15 ggc agc ggc gcc ttc ccg ccc ggc cac ttc aag gac ccc aag cgg ctg      96
Gly Ser Gly Ala Phe Pro Pro Gly His Phe Lys Asp Pro Lys Arg Leu
            20                  25                  30 tac tgc aaa aac ggg ggc ttc ttc ctg cgc atc cac ccc gac ggc cga     144
Tyr Cys Lys Asn Gly Gly Phe Phe Leu Arg Ile His Pro Asp Gly Arg
        35                  40                  45 gtt gac ggg gtc cgg gag aag agc gac cct cac atc aag cta caa ctt     192
Val Asp Gly Val Arg Glu Lys Ser Asp Pro His Ile Lys Leu Gln Leu
    50                  55                  60 caa gca gaa gag aga gga gtt gtg tct atc aaa gga gtg tgt gct aac     240
Gln Ala Glu Glu Arg Gly Val Val Ser Ile Lys Gly Val Cys Ala Asn
65                  70                  75                  80 cgt tac ctg gct atg aag gaa gat gga aga tta ctg gct tct aaa tgt     288
Arg Tyr Leu Ala Met Lys Glu Asp Gly Arg Leu Leu Ala Ser Lys Cys
                85                  90                  95 gtt acg gat gag tgt ttc ttt ttt gaa cga ttg gaa tct aat aac tac     336
Val Thr Asp Glu Cys Phe Phe Phe Glu Arg Leu Glu Ser Asn Asn Tyr
            100                 105                 110 aat act tac cgg tca agg aaa tac acc agt tgg tat gtg gca ctg aaa     384
Asn Thr Tyr Arg Ser Arg Lys Tyr Thr Ser Trp Tyr Val Ala Leu Lys
        115                 120                 125 cga act ggg cag tat aaa ctt gga tcc aaa aca gga cct ggg cag aaa     432
Arg Thr Gly Gln Tyr Lys Leu Gly Ser Lys Thr Gly Pro Gly Gln Lys
    130                 135                 140 gct ata ctt ttt ctt cca atg tct gct aag agc                         465
Ala Ile Leu Phe Leu Pro Met Ser Ala Lys Ser
145                 150                 155

<210> SEQ ID NO 2
<211> LENGTH: 155
<212> TYPE: PRT
<213> ORGANISM: Homo sapiens

<400> SEQUENCE: 2

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
```

```
                    130                 135                 140
Ala Ile Leu Phe Leu Pro Met Ser Ala Lys Ser
145                 150                 155

<210> SEQ ID NO 3
<211> LENGTH: 465
<212> TYPE: DNA
<213> ORGANISM: Mus musculus
<220> FEATURE:
<221> NAME/KEY: CDS
<222> LOCATION: (1)..(465)

<400> SEQUENCE: 3 atg gct gcc agc ggc atc acc tcg ctt ccc gca ctg ccg gag gac ggc      48
Met Ala Ala Ser Gly Ile Thr Ser Leu Pro Ala Leu Pro Glu Asp Gly
1               5                   10                  15 ggc gcc gcc ttc cca cca ggc cac ttc aag gac ccc aag cgg ctc tac      96
Gly Ala Ala Phe Pro Pro Gly His Phe Lys Asp Pro Lys Arg Leu Tyr
                20                  25                  30 tgc aag aac ggc ggc ttc ttc ctg cgc atc cat ccc gac ggc cgc gtg     144
Cys Lys Asn Gly Gly Phe Phe Leu Arg Ile His Pro Asp Gly Arg Val
            35                  40                  45 gat ggc gtc cgc gag aag agc gac cca cac gtc aaa cta caa ctc caa     192
Asp Gly Val Arg Glu Lys Ser Asp Pro His Val Lys Leu Gln Leu Gln
        50                  55                  60 gca gaa gag aga gga gtt gtg tct atc aag gga gtg tgt gcc aac cgg     240
Ala Glu Glu Arg Gly Val Val Ser Ile Lys Gly Val Cys Ala Asn Arg
65                  70                  75                  80 tac ctt gct atg aag gaa gat gga cgg ctg ctg gct tct aag tgt gtt     288
Tyr Leu Ala Met Lys Glu Asp Gly Arg Leu Leu Ala Ser Lys Cys Val
                85                  90                  95 aca gaa gag tgt ttc ttc ttt gaa cga ctg gaa tct aat aac tac aat     336
Thr Glu Glu Cys Phe Phe Phe Glu Arg Leu Glu Ser Asn Asn Tyr Asn
                100                 105                 110 act tac cgg tca cgg aaa tac tcc agt tgg tat gtg gca ctg aaa cga     384
Thr Tyr Arg Ser Arg Lys Tyr Ser Ser Trp Tyr Val Ala Leu Lys Arg
            115                 120                 125 act ggg cag tat aaa ctc gga tcc aaa acg gga cct gga cag aag gcc     432
Thr Gly Gln Tyr Lys Leu Gly Ser Lys Thr Gly Pro Gly Gln Lys Ala
        130                 135                 140 ata ctg ttt ctt cca atg tct gct aag agc tga                         465
Ile Leu Phe Leu Pro Met Ser Ala Lys Ser
145                 150

<210> SEQ ID NO 4
<211> LENGTH: 154
<212> TYPE: PRT
<213> ORGANISM: Mus musculus

<400> SEQUENCE: 4

Met Ala Ala Ser Gly Ile Thr Ser Leu Pro Ala Leu Pro Glu Asp Gly
1               5                   10                  15

Gly Ala Ala Phe Pro Pro Gly His Phe Lys Asp Pro Lys Arg Leu Tyr
                20                  25                  30

Cys Lys Asn Gly Gly Phe Phe Leu Arg Ile His Pro Asp Gly Arg Val
            35                  40                  45

Asp Gly Val Arg Glu Lys Ser Asp Pro His Val Lys Leu Gln Leu Gln
        50                  55                  60

Ala Glu Glu Arg Gly Val Val Ser Ile Lys Gly Val Cys Ala Asn Arg
65                  70                  75                  80
```

```
Tyr Leu Ala Met Lys Glu Asp Gly Arg Leu Ala Ser Lys Cys Val
             85                  90                  95

Thr Glu Glu Cys Phe Phe Glu Arg Leu Glu Ser Asn Asn Tyr Asn
            100                 105                 110

Thr Tyr Arg Ser Arg Lys Tyr Ser Ser Trp Tyr Val Ala Leu Lys Arg
            115                 120                 125

Thr Gly Gln Tyr Lys Leu Gly Ser Lys Thr Gly Pro Gly Gln Lys Ala
        130                 135                 140

Ile Leu Phe Leu Pro Met Ser Ala Lys Ser
145                 150
```

<210> SEQ ID NO 5
<211> LENGTH: 468
<212> TYPE: DNA
<213> ORGANISM: Homo sapiens
<220> FEATURE:
<221> NAME/KEY: CDS
<222> LOCATION: (1)..(468)

<400> SEQUENCE: 5

```
atg gct gaa ggg gaa atc acc acc ttc aca gcc ctg acc gag aag ttt      48
Met Ala Glu Gly Glu Ile Thr Thr Phe Thr Ala Leu Thr Glu Lys Phe
1               5                   10                  15 aat ctg cct cca ggg aat tac aag aag ccc aaa ctc ctc tac tgt agc      96
Asn Leu Pro Pro Gly Asn Tyr Lys Lys Pro Lys Leu Leu Tyr Cys Ser
                20                  25                  30 aac ggg ggc cac ttc ctg agg atc ctt ccg gat ggc aca gtg gat ggg     144
Asn Gly Gly His Phe Leu Arg Ile Leu Pro Asp Gly Thr Val Asp Gly
            35                  40                  45 aca agg gac agg agc gac cag cac att cag ctg cag ctc agt gcg gaa     192
Thr Arg Asp Arg Ser Asp Gln His Ile Gln Leu Gln Leu Ser Ala Glu
        50                  55                  60 agc gtg ggg gag gtg tat ata aag agt acc gag act ggc cag tac ttg     240
Ser Val Gly Glu Val Tyr Ile Lys Ser Thr Glu Thr Gly Gln Tyr Leu
65                  70                  75                  80 gcc atg gac acc gac ggg ctt tta tac ggc tca cag aca cca aat gag     288
Ala Met Asp Thr Asp Gly Leu Leu Tyr Gly Ser Gln Thr Pro Asn Glu
                85                  90                  95 gaa tgt ttg ttc ctg gaa agg ctg gag gag aac cat tac aac acc tat     336
Glu Cys Leu Phe Leu Glu Arg Leu Glu Glu Asn His Tyr Asn Thr Tyr
            100                 105                 110 ata tcc aag aag cat gca gag aag aat tgg ttt gtt ggc ctc aag aag     384
Ile Ser Lys Lys His Ala Glu Lys Asn Trp Phe Val Gly Leu Lys Lys
        115                 120                 125 aat ggg agc tgc aaa cgc ggt cct cgg act cac tat ggc cag aaa gca     432
Asn Gly Ser Cys Lys Arg Gly Pro Arg Thr His Tyr Gly Gln Lys Ala
130                 135                 140 atc ttg ttt ctc ccc ctg cca gtc tct tct gat taa                     468
Ile Leu Phe Leu Pro Leu Pro Val Ser Ser Asp
145                 150                 155
```

<210> SEQ ID NO 6
<211> LENGTH: 155
<212> TYPE: PRT
<213> ORGANISM: Homo sapiens

<400> SEQUENCE: 6

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
                20                  25                  30
```

```
Asn Gly Gly His Phe Leu Arg Ile Leu Pro Asp Gly Thr Val Asp Gly
         35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

<210> SEQ ID NO 7
<211> LENGTH: 468
<212> TYPE: DNA
<213> ORGANISM: Mus musculus
<220> FEATURE:
<221> NAME/KEY: CDS
<222> LOCATION: (1)..(468)

<400> SEQUENCE: 7
```

| | | | | | | | | | | | | | | | | |
|---|---|---|---|---|---|---|---|---|---|---|---|---|---|---|---|---|
| atg | gct | gaa | ggg | gag | atc | aca | acc | ttc | gca | gcc | ctg | acc | gag | agg | ttc | 48 |
| Met | Ala | Glu | Gly | Glu | Ile | Thr | Thr | Phe | Ala | Ala | Leu | Thr | Glu | Arg | Phe | |
| 1 | | | | 5 | | | | | 10 | | | | | 15 | | |
| aac | ctg | cct | cta | gga | aac | tac | aaa | aag | ccc | aaa | ctg | ctc | tac | tgc | agc | 96 |
| Asn | Leu | Pro | Leu | Gly | Asn | Tyr | Lys | Lys | Pro | Lys | Leu | Leu | Tyr | Cys | Ser | |
| | | | | 20 | | | | | 25 | | | | | 30 | | |
| aac | ggg | ggc | cac | ttc | ttg | agg | atc | ctt | cct | gat | ggc | acc | gtg | gat | ggg | 144 |
| Asn | Gly | Gly | His | Phe | Leu | Arg | Ile | Leu | Pro | Asp | Gly | Thr | Val | Asp | Gly | |
| | | | | 35 | | | | | 40 | | | | | 45 | | |
| aca | agg | gac | agg | agc | gac | cag | cac | att | cag | ctg | cag | ctc | agt | gcg | gaa | 192 |
| Thr | Arg | Asp | Arg | Ser | Asp | Gln | His | Ile | Gln | Leu | Gln | Leu | Ser | Ala | Glu | |
| | 50 | | | | | 55 | | | | | 60 | | | | | |
| agt | gcg | ggc | gaa | gtg | tat | ata | aag | ggt | acg | gag | acc | ggc | cag | tac | ttg | 240 |
| Ser | Ala | Gly | Glu | Val | Tyr | Ile | Lys | Gly | Thr | Glu | Thr | Gly | Gln | Tyr | Leu | |
| 65 | | | | | 70 | | | | | 75 | | | | | 80 | |
| gcc | atg | gac | acc | gaa | ggg | ctt | tta | tac | ggc | tcg | cag | aca | cca | aat | gag | 288 |
| Ala | Met | Asp | Thr | Glu | Gly | Leu | Leu | Tyr | Gly | Ser | Gln | Thr | Pro | Asn | Glu | |
| | | | | 85 | | | | | 90 | | | | | 95 | | |
| gaa | tgt | ctg | ttc | ctg | gaa | agg | ctg | gaa | gaa | aac | cat | tat | aac | act | tac | 336 |
| Glu | Cys | Leu | Phe | Leu | Glu | Arg | Leu | Glu | Glu | Asn | His | Tyr | Asn | Thr | Tyr | |
| | | | | 100 | | | | | 105 | | | | | 110 | | |
| acc | tcc | aag | aag | cat | gcg | gag | aag | aac | tgg | ttt | gtg | ggc | ctc | aag | aag | 384 |
| Thr | Ser | Lys | Lys | His | Ala | Glu | Lys | Asn | Trp | Phe | Val | Gly | Leu | Lys | Lys | |
| | | | 115 | | | | | 120 | | | | | 125 | | | |
| aac | ggg | agc | tgt | aag | cgc | ggt | cct | cgg | act | cac | tat | ggc | cag | aaa | gcc | 432 |
| Asn | Gly | Ser | Cys | Lys | Arg | Gly | Pro | Arg | Thr | His | Tyr | Gly | Gln | Lys | Ala | |
| | | 130 | | | | | 135 | | | | | 140 | | | | |
| atc | ttg | ttt | ctg | ccc | ctc | ccg | gtg | tct | tct | gac | tag | | | | | 468 |
| Ile | Leu | Phe | Leu | Pro | Leu | Pro | Val | Ser | Ser | Asp | | | | | | |
| 145 | | | | 150 | | | | 155 | | | | | | | | |

```
<210> SEQ ID NO 8
<211> LENGTH: 155
```

```
<212> TYPE: PRT
<213> ORGANISM: Mus musculus

<400> SEQUENCE: 8

Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 9
<211> LENGTH: 158
<212> TYPE: PRT
<213> ORGANISM: Artificial Sequence
<220> FEATURE:
<223> OTHER INFORMATION: FGF2/FGF1 chimeric protein sequence (FGF24)
<220> FEATURE:
<221> NAME/KEY: MISC_FEATURE
<222> LOCATION: (1)..(21)
<223> OTHER INFORMATION: FGF2 portion
<220> FEATURE:
<221> NAME/KEY: MISC_FEATURE
<222> LOCATION: (22)..(158)
<223> OTHER INFORMATION: FGF1 portion

<400> SEQUENCE: 9

Met Ala Ala Gly Ser Ile Thr Thr Leu Pro Ala Leu Pro Glu Asp Gly
1               5                   10                  15

Gly Ser Gly Ala Phe Pro Pro Gly Asn Tyr Lys Lys Pro Lys Leu Leu
            20                  25                  30

Tyr Cys Ser Asn Gly Gly His Phe Leu Arg Ile Leu Pro Asp Gly Thr
        35                  40                  45

Val Asp Gly Thr Arg Asp Arg Ser Asp Gln His Ile Gln Leu Gln Leu
    50                  55                  60

Ser Ala Glu Ser Val Gly Glu Val Tyr Ile Lys Ser Thr Glu Thr Gly
65                  70                  75                  80

Gln Tyr Leu Ala Met Asp Thr Asp Gly Leu Leu Tyr Gly Ser Gln Thr
                85                  90                  95

Pro Asn Glu Glu Cys Leu Phe Leu Glu Arg Leu Glu Glu Asn His Tyr
            100                 105                 110

Asn Thr Tyr Ile Ser Lys Lys His Ala Glu Lys Asn Trp Phe Val Gly
        115                 120                 125

Leu Lys Lys Asn Gly Ser Cys Lys Arg Gly Pro Arg Thr His Tyr Gly
    130                 135                 140
```

```
Gln Lys Ala Ile Leu Phe Leu Pro Leu Pro Val Ser Ser Asp
145                 150                 155

<210> SEQ ID NO 10
<211> LENGTH: 158
<212> TYPE: PRT
<213> ORGANISM: Artificial Sequence
<220> FEATURE:
<223> OTHER INFORMATION: FGF2/FGF1 chimeric protein sequence (FGF24.1)
<220> FEATURE:
<221> NAME/KEY: MISC_FEATURE
<222> LOCATION: (1)..(21)
<223> OTHER INFORMATION: FGF2 portion
<220> FEATURE:
<221> NAME/KEY: MISC_FEATURE
<222> LOCATION: (22)..(158)
<223> OTHER INFORMATION: FGF1 portion

<400> SEQUENCE: 10

Met Ala Ala Gly Ser Ile Thr Thr Leu Pro Ala Leu Pro Glu Asp Gly
1               5                   10                  15

Gly Ser Phe Ala Phe Pro Pro Gly Asn Tyr Lys Lys Pro Lys Leu Leu
            20                  25                  30

Tyr Cys Ser Asn Gly Gly His Phe Leu Arg Ile Leu Pro Asp Gly Thr
        35                  40                  45

Val Asp Gly Thr Arg Asp Arg Ser Asp Gln His Ile Gln Leu Gln Leu
    50                  55                  60

Ser Ala Glu Ser Val Gly Glu Val Tyr Ile Lys Ser Thr Glu Thr Gly
65                  70                  75                  80

Gln Tyr Leu Ala Met Asp Thr Asp Gly Leu Leu Tyr Gly Ser Gln Thr
                85                  90                  95

Pro Asn Glu Glu Cys Leu Phe Leu Glu Arg Leu Glu Glu Asn His Tyr
            100                 105                 110

Asn Thr Tyr Ile Ser Lys Lys His Ala Glu Lys Asn Trp Phe Val Gly
        115                 120                 125

Leu Lys Lys Asn Gly Ser Cys Lys Arg Gly Pro Arg Thr His Tyr Gly
    130                 135                 140

Gln Lys Ala Ile Leu Phe Leu Pro Leu Pro Val Ser Ser Asp
145                 150                 155

<210> SEQ ID NO 11
<211> LENGTH: 158
<212> TYPE: PRT
<213> ORGANISM: Artificial Sequence
<220> FEATURE:
<223> OTHER INFORMATION: FGF2/FGF1 chimeric protein sequence (FGF24.2)
<220> FEATURE:
<221> NAME/KEY: MISC_FEATURE
<222> LOCATION: (1)..(21)
<223> OTHER INFORMATION: FGF2 portion
<220> FEATURE:
<221> NAME/KEY: MISC_FEATURE
<222> LOCATION: (22)..(158)
<223> OTHER INFORMATION: FGF1 portion

<400> SEQUENCE: 11

Met Ala Ala Gly Ser Ile Thr Thr Leu Pro Ala Leu Pro Glu Asp Gly
1               5                   10                  15

Gly Ser Phe Asn Leu Pro Pro Gly Asn Tyr Lys Lys Pro Lys Leu Leu
            20                  25                  30

Tyr Cys Ser Asn Gly Gly His Phe Leu Arg Ile Leu Pro Asp Gly Thr
        35                  40                  45
```

Val Asp Gly Thr Arg Asp Arg Ser Asp Gln His Ile Gln Leu Gln Leu
    50                  55                  60
Ser Ala Glu Ser Val Gly Glu Val Tyr Ile Lys Ser Thr Glu Thr Gly
 65                  70                  75                  80
Gln Tyr Leu Ala Met Asp Thr Asp Gly Leu Leu Tyr Gly Ser Gln Thr
                 85                  90                  95
Pro Asn Glu Glu Cys Leu Phe Leu Glu Arg Leu Glu Glu Asn His Tyr
            100                 105                 110
Asn Thr Tyr Ile Ser Lys Lys His Ala Glu Lys Asn Trp Phe Val Gly
                115                 120                 125
Leu Lys Lys Asn Gly Ser Cys Lys Arg Gly Pro Arg Thr His Tyr Gly
            130                 135                 140
Gln Lys Ala Ile Leu Phe Leu Pro Leu Pro Val Ser Ser Asp
145                 150                 155

<210> SEQ ID NO 12
<211> LENGTH: 149
<212> TYPE: PRT
<213> ORGANISM: Artificial Sequence
<220> FEATURE:
<223> OTHER INFORMATION: FGF2/FGF1 chimeric protein sequence (FGF24
      without the MAAGSITTL signal sequence)
<220> FEATURE:
<221> NAME/KEY: MISC_FEATURE
<222> LOCATION: (1)..(12)
<223> OTHER INFORMATION: FGF2 portion
<220> FEATURE:
<221> NAME/KEY: MISC_FEATURE
<222> LOCATION: (13)..(149)
<223> OTHER INFORMATION: FGF1 portion

<400> SEQUENCE: 12

Pro Ala Leu Pro Glu Asp Gly Gly Ser Gly Ala Phe Pro Pro Gly Asn
  1               5                  10                  15
Tyr Lys Lys Pro Lys Leu Leu Tyr Cys Ser Asn Gly Gly His Phe Leu
                 20                  25                  30
Arg Ile Leu Pro Asp Gly Thr Val Asp Gly Thr Arg Asp Arg Ser Asp
                 35                  40                  45
Gln His Ile Gln Leu Gln Leu Ser Ala Glu Ser Val Gly Glu Val Tyr
    50                  55                  60
Ile Lys Ser Thr Glu Thr Gly Gln Tyr Leu Ala Met Asp Thr Asp Gly
 65                  70                  75                  80
Leu Leu Tyr Gly Ser Gln Thr Pro Asn Glu Glu Cys Leu Phe Leu Glu
                 85                  90                  95
Arg Leu Glu Glu Asn His Tyr Asn Thr Tyr Ile Ser Lys Lys His Ala
            100                 105                 110
Glu Lys Asn Trp Phe Val Gly Leu Lys Lys Asn Gly Ser Cys Lys Arg
                115                 120                 125
Gly Pro Arg Thr His Tyr Gly Gln Lys Ala Ile Leu Phe Leu Pro Leu
            130                 135                 140
Pro Val Ser Ser Asp
145

<210> SEQ ID NO 13
<211> LENGTH: 150
<212> TYPE: PRT
<213> ORGANISM: Artificial Sequence
<220> FEATURE:
<223> OTHER INFORMATION: FGF2/FGF1 chimeric protein sequence (FGF24 with
      an N-terminal M instead of the MAAGSITTL signal sequence)
<220> FEATURE:

<220> FEATURE:
<221> NAME/KEY: MISC_FEATURE
<222> LOCATION: (1)..(13)
<223> OTHER INFORMATION: FGF2 portion
<220> FEATURE:
<221> NAME/KEY: MISC_FEATURE
<222> LOCATION: (14)..(140)
<223> OTHER INFORMATION: FGF1 portion

<400> SEQUENCE: 13

```
Met Pro Ala Leu Pro Glu Asp Gly Gly Ser Gly Ala Phe Pro Pro Gly
 1               5                  10                  15

Asn Tyr Lys Lys Pro Lys Leu Leu Tyr Cys Ser Asn Gly Gly His Phe
             20                  25                  30

Leu Arg Ile Leu Pro Asp Gly Thr Val Asp Gly Thr Arg Asp Arg Ser
         35                  40                  45

Asp Gln His Ile Gln Leu Gln Leu Ser Ala Glu Ser Val Gly Glu Val
     50                  55                  60

Tyr Ile Lys Ser Thr Glu Thr Gly Gln Tyr Leu Ala Met Asp Thr Asp
 65                  70                  75                  80

Gly Leu Leu Tyr Gly Ser Gln Thr Pro Asn Glu Glu Cys Leu Phe Leu
                 85                  90                  95

Glu Arg Leu Glu Glu Asn His Tyr Asn Thr Tyr Ile Ser Lys Lys His
            100                 105                 110

Ala Glu Lys Asn Trp Phe Val Gly Leu Lys Lys Asn Gly Ser Cys Lys
        115                 120                 125

Arg Gly Pro Arg Thr His Tyr Gly Gln Lys Ala Ile Leu Phe Leu Pro
    130                 135                 140

Leu Pro Val Ser Ser Asp
145                 150
```

<210> SEQ ID NO 14
<211> LENGTH: 477
<212> TYPE: DNA
<213> ORGANISM: Artificial Sequence
<220> FEATURE:
<223> OTHER INFORMATION: FGF24 coding sequence

<400> SEQUENCE: 14

```
atggccgctg gctcaatcac gacgctgccg gctctgccgg aagatggtgg ctcaggtgcc    60
tttccgccgg gtaactacaa aaaaccgaaa ctgctgtatt gcagcaacgg cggtcatttt   120
ctgcgtattc tgccggatgg caccgtcgac ggtacgcgtg atcgcagtga ccagcacatt   180
cagctgcaac tgagcgcgga atctgtgggt gaagtttata tcaaatcaac cgaaacgggc   240
cagtacctgg ccatggatac cgacggcctg ctgtacggtt cgcaaacgcc gaatgaagaa   300
tgcctgtttc tggaacgtct ggaagaaaac cattacaaca cctacatcag taaaaaacac   360
gcggagaaaa actggttcgt tggcctgaag aaaaacggtt cctgtaaacg cggcccgcgc   420
acccattacg gtcaaaaagc cattctgttt ctgccgctgc cggtttcgtc gactaa       477
```

<210> SEQ ID NO 15
<211> LENGTH: 477
<212> TYPE: DNA
<213> ORGANISM: Artificial Sequence
<220> FEATURE:
<223> OTHER INFORMATION: FGF24.1 coding sequence

<400> SEQUENCE: 15

```
atggccgctg gctcaatcac gacgctgccg gctctgccgg aagatggtgg ctcattcgcc    60
tttccgccgg gtaactacaa aaaaccgaaa ctgctgtatt gcagcaacgg cggtcatttt   120
```

```
ctgcgtattc tgccggatgg caccgtcgac ggtacgcgtg atcgcagtga ccagcacatt        180
cagctgcaac tgagcgcgga atctgtgggt gaagtttata tcaaatcaac cgaaacgggc        240
cagtacctgg ccatggatac cgacggcctg ctgtacggtt cgcaaacgcc gaatgaagaa        300
tgcctgtttc tggaacgtct ggaagaaaac cattacaaca cctacatcag taaaaaacac        360
gcggagaaaa actggttcgt tggcctgaag aaaaacggtt cctgtaaacg cggcccgcgc        420
acccattacg gtcaaaaagc cattctgttt ctgccgctgc cggtttcgtc cgactaa            477
```

```
<210> SEQ ID NO 16
<211> LENGTH: 477
<212> TYPE: DNA
<213> ORGANISM: Artificial Sequence
<220> FEATURE:
<223> OTHER INFORMATION: FGF24.2 coding sequence

<400> SEQUENCE: 16
```

```
atggccgctg gctcaatcac gacgctgccg gctctgccgg aagatggtgg ctcattcaac         60
ctgccgccgg gtaactacaa aaaaccgaaa ctgctgtatt gcagcaacgg cggtcatttt        120
ctgcgtattc tgccggatgg caccgtcgac ggtacgcgtg atcgcagtga ccagcacatt        180
cagctgcaac tgagcgcgga atctgtgggt gaagtttata tcaaatcaac cgaaacgggc        240
cagtacctgg ccatggatac cgacggcctg ctgtacggtt cgcaaacgcc gaatgaagaa        300
tgcctgtttc tggaacgtct ggaagaaaac cattacaaca cctacatcag taaaaaacac        360
gcggagaaaa actggttcgt tggcctgaag aaaaacggtt cctgtaaacg cggcccgcgc        420
acccattacg gtcaaaaagc cattctgttt ctgccgctgc cggtttcgtc cgactaa            477
```

```
<210> SEQ ID NO 17
<211> LENGTH: 468
<212> TYPE: DNA
<213> ORGANISM: Artificial Sequence
<220> FEATURE:
<223> OTHER INFORMATION: human FGF1 codon optimized for improved
      expression in bacteria
<220> FEATURE:
<221> NAME/KEY: CDS
<222> LOCATION: (1)..(468)

<400> SEQUENCE: 17
```

```
atg gct gaa ggc gaa atc acg acg ttc acc gct ctg acg gaa aaa ttc         48
Met Ala Glu Gly Glu Ile Thr Thr Phe Thr Ala Leu Thr Glu Lys Phe
1               5                   10                  15 aat ctg ccg ccg ggt aac tac aaa aaa ccg aaa ctg ctg tat tgc agc         96
Asn Leu Pro Pro Gly Asn Tyr Lys Lys Pro Lys Leu Leu Tyr Cys Ser
            20                  25                  30 aac ggc ggt cat ttt ctg cgt att ctg ccg gat ggc acc gtc gac ggt        144
Asn Gly Gly His Phe Leu Arg Ile Leu Pro Asp Gly Thr Val Asp Gly
        35                  40                  45 acg cgt gat cgc agt gac cag cac att cag ctg caa ctg agc gcg gaa        192
Thr Arg Asp Arg Ser Asp Gln His Ile Gln Leu Gln Leu Ser Ala Glu
    50                  55                  60 tct gtg ggt gaa gtt tat atc aaa tca acc gaa acg ggc cag tac ctg        240
Ser Val Gly Glu Val Tyr Ile Lys Ser Thr Glu Thr Gly Gln Tyr Leu
65                  70                  75                  80 gcc atg gat acc gac ggc ctg ctg tac ggt tcg caa acg ccg aat gaa        288
Ala Met Asp Thr Asp Gly Leu Leu Tyr Gly Ser Gln Thr Pro Asn Glu
                85                  90                  95 gaa tgc ctg ttt ctg gaa cgt ctg gaa gaa aac cat tac aac acc tac        336
Glu Cys Leu Phe Leu Glu Arg Leu Glu Glu Asn His Tyr Asn Thr Tyr
```

-continued

```
                        100                 105                 110
atc agt aaa aaa cac gcg gag aaa aac tgg ttc gtt ggc ctg aag aaa      384
Ile Ser Lys Lys His Ala Glu Lys Asn Trp Phe Val Gly Leu Lys Lys
        115                 120                 125 aac ggt tcc tgt aaa cgc ggc ccg cgc acg cat tac ggt cag aaa gca      432
Asn Gly Ser Cys Lys Arg Gly Pro Arg Thr His Tyr Gly Gln Lys Ala
    130                 135                 140 atc ctg ttc ctg ccg ctg ccg gtc tcc tcc gac taa                      468
Ile Leu Phe Leu Pro Leu Pro Val Ser Ser Asp
145                 150                 155

<210> SEQ ID NO 18
<211> LENGTH: 155
<212> TYPE: PRT
<213> ORGANISM: Artificial Sequence
<220> FEATURE:
<223> OTHER INFORMATION: Synthetic Construct

<400> SEQUENCE: 18

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```